(12) United States Patent
Day et al.

(10) Patent No.: US 9,561,250 B2
(45) Date of Patent: *Feb. 7, 2017

(54) SCAFFOLD FOR TISSUE REGENERATION IN MAMMALS

(71) Applicant: The Curators of the University of Missouri, Columbia, MO (US)

(72) Inventors: Delbert E. Day, Rolla, MO (US);
Steven B. Jung, Rolla, MO (US);
Roger F. Brown, Rolla, MO (US)

(73) Assignee: The Curators of the University of Missouri, Columbia, MO (US)

( * ) Notice: Subject to any disclaimer, the term of this patent is extended or adjusted under 35 U.S.C. 154(b) by 178 days.

This patent is subject to a terminal disclaimer.

(21) Appl. No.: 13/936,702

(22) Filed: Jul. 8, 2013

(65) Prior Publication Data

US 2014/0037756 A1 Feb. 6, 2014

Related U.S. Application Data

(63) Continuation of application No. 12/504,489, filed on Jul. 16, 2009, now Pat. No. 8,481,066.

(51) Int. Cl.
| | | |
|---|---|---|
| A61F 2/00 | (2006.01) |
| A61K 33/22 | (2006.01) |
| A61L 27/10 | (2006.01) |
| A61L 27/56 | (2006.01) |
| C03C 3/14 | (2006.01) |
| C03C 3/19 | (2006.01) |
| C03C 4/00 | (2006.01) |
| C03C 11/00 | (2006.01) |
| C03C 13/00 | (2006.01) |

(52) U.S. Cl.
CPC ............... *A61K 33/22* (2013.01); *A61L 27/10* (2013.01); *A61L 27/56* (2013.01); *C03C 3/14* (2013.01); *C03C 3/19* (2013.01); *C03C 4/0007* (2013.01); *C03C 11/00* (2013.01); *C03C 13/00* (2013.01)

(58) Field of Classification Search
USPC ....................................................... 424/423
See application file for complete search history.

(56) References Cited

U.S. PATENT DOCUMENTS

| | | |
|---|---|---|
| 413,597 A | 10/1889 | Burleigh |
| 4,243,567 A | 1/1981 | Potter |
| 4,250,277 A | 2/1981 | Maries et al. |
| 4,842,620 A | 6/1989 | Hammel et al. |
| 4,853,001 A | 8/1989 | Hammel |
| 4,933,307 A | 6/1990 | Marshall et al. |
| 5,204,106 A | 4/1993 | Schepers et al. |
| 5,691,256 A | 11/1997 | Taguchi et al. |
| 6,143,318 A | 11/2000 | Gilchrist et al. |
| 6,358,531 B1 | 3/2002 | Day et al. |
| 6,379,648 B1 | 4/2002 | Day et al. |
| 6,447,805 B1 | 9/2002 | Healy |
| 6,709,744 B1 | 3/2004 | Day et al. |
| 2002/0160175 A1 | 10/2002 | Pirhonen |
| 2004/0078077 A1 | 4/2004 | Binette et al. |
| 2004/0170692 A1 | 9/2004 | Day et al. |
| 2004/0253321 A1 | 12/2004 | Fechner et al. |
| 2005/0013873 A1 | 1/2005 | Fechner et al. |
| 2005/0021152 A1 | 1/2005 | Ogle et al. |
| 2005/0064193 A1 | 3/2005 | Fechner et al. |
| 2005/0102035 A1 | 5/2005 | Grundei |
| 2005/0169967 A1 | 8/2005 | Gilchrist et al. |
| 2005/0255159 A1 | 11/2005 | Hyers et al. |
| 2006/0233887 A1 | 10/2006 | Day |
| 2008/0044488 A1 | 2/2008 | Zimmer et al. |
| 2008/0066495 A1 | 3/2008 | Moimas et al. |
| 2009/0208428 A1 | 8/2009 | Hill et al. |
| 2009/0276056 A1 | 11/2009 | Bose et al. |

FOREIGN PATENT DOCUMENTS

| | | |
|---|---|---|
| DE | 102004021700 A1 | 11/2005 |
| EP | 1716873 | 11/2006 |
| GB | 2037735 | 7/1980 |
| WO | 80/02378 | 11/1980 |
| WO | 9854104 | 12/1998 |
| WO | 2007124511 | 11/2007 |
| WO | 2007/144662 | 12/2007 |

OTHER PUBLICATIONS

Borden (Biomaterials 24 (2003) 597-609).*
S. Hesaraki et al., "Montmorillonite-added calcium phosphate bioceramic foams" (2008; online Nov. 20, 2007) Key Engineering Materials, vols. 361-363, pp. 111-114.
C. Mazilu et al., "Bioactive vitroceramic utilized in modern reparatory medicine" (Apr. 2006) Journal of Optoelectronics and Advanced Materials, vol. 8, No. 2, p. 741-744.
Conzone et al., Preparation and properties of porous microspheres made from borate glass, J. of Biomed. Mater. Res. Part 88A: 531-542 (2009) (published online Feb. 27, 2008 www.interscience.wiley.com).
Rahaman et al. (Advances in Bioceramics and Biocomposites; The American Ceramic Society; 2005).
Liang and Russel (J Mater Sci 41 (2006) 3787-3792).
Huang et al. (J. Am. Ceram. Soc., 91 [6] 1898-1904 (2008); first published online Apr. 2, 2008).
Neel et al. (Biomaterials 26 (2005) 2247-2254).
Yao, Aihua et al., "In Vitro Bioactive Characteristics of Borate-Based Glasses with Controllable Degradation Behavior", Journal of the American Ceramic Society, vol. 90 Issue 1, Nov. 7, 2006, pp. 303-306.

(Continued)

*Primary Examiner* — Devang Thakor
(74) *Attorney, Agent, or Firm* — Senniger Powers LLP

(57) ABSTRACT

A three-dimensional scaffold with interconnected pores for repair of tissue comprising a scaffold body for structural support of the tissue scaffold, where the scaffold body comprises scaffold body components bonded to each other and made from component materials comprising about 40 to about 90 wt % $B_2O_3$, and two or more other oxides, wherein the scaffold body has a porosity between about 15 and about 90 vol %.

23 Claims, 23 Drawing Sheets

(56) References Cited

OTHER PUBLICATIONS

Ning, Jia et al., "Synthesis and in Vitro Bioactivity of a Borate-Based Bioglass", Materials Letters, vol. 61, Issue 30, Dec. 2007, pp. 5223-5226.

Liang, Wen, "Bioactive Comparison of a Borate, Phosphate and Silicate Glass", Journal of Materials Research, vol. 21, Issue 1, 2005, pp. 125-131.

Jung, Steven, "Conversion Kinetics of Silicate, Borosilicate, and Borate Bioactive Glasses to Hydroxyapatite", Physics and Chemistry of Glasses—European Journal of Glass Science and Technology Part B, Apr. 2009, vol. 50, No. 2, pp. 85-88.

Liang, Wen et al., "Bioactive Borate Glass Scaffold for Bone Tissue Engineering", Journal of Non-Crystalline Solids, Journal of Non-Crystalline Solids, vol. 354, Issues 15-16, Mar. 15, 2008, pp. 1690-1696.

Liu et al., "Bioactive borosilicate glass scaffolds: improvement on the strength of glass-based scaffolds for tissue engineering", Journal of Material Science: Materials in Medicine, vol. 20, No. 1, Sep. 2008, pp. 365-372.

Rahaman et al., "Preparation and Bioactive Characteristics of Porous Borate Glass Substrates", Ceramic Engineering and Science Proceedings, vol. 26, No. 6, 2005, pp. 3-10.

Yao et al., "Preparation of Bioactive Glasses with Controllable Degradation Behavior and their Bioactive Characterization", Chinese Science Bulletin, vol. 52, No. 2, Jan. 2007, pp. 272-276.

Huang et al., "Strength of Hollow Hydroxyapatite Microspheres Prepared by a Glass Conversion Process", Journal of Materials Science: Materials in Medicine, vol. 20, No. 1, Aug. 14, 2008, pp. 123-129.

International Search Report, PCT/2010/41773, Sep. 7, 2010, 4 pages.

Written Opinion, PCT/2010/41773, Sep. 7, 2010, 6 pages.

Li et al., "An Investigation of Bioactive Glass Powders by Sol-Gel Processing," [online abstract], Journal of Applied Biomaterials, 1991, vol. 2, Issue 4, pp. 231-239.

"A New Generation of Bioactive Materials Useful for Bone and Tissue Repair," Missouri University of Science and Technology, Sep. 13, 2010, <http://www.ibridgenetwork.org/file.sub.--records/show/8512>.

Day, R.M., Bioactive Glass Stimulates the Secretion of Angiogenic Growth Factors and Angiogenesis in Vitro, 2005, Tissue Engineering, vol. 11, No. 516, pp. 768-777.

Kokubo et al., How useful is SBF in predicting in vivo bone activity?, 2006, Biomaterials 27 (2006) 2907-2915.

International Preliminary Report on Patentability, PCT/US2010/041773, dated Jan. 17, 2012, 8 pages.

Marina Nathalie Camille Richard, "Bioactive Behavior of Borate Glass", Presented to the Faculty of the Graduate School of the University of Missouri-Rolla, Apr. 2000, pp. 1-139.

Holmes et al., "Protected Bone Regeneration", Scientific Data Series in Resorbable Fixation, Medtronic Sofamor Danek, 2001, 11 pages.

* cited by examiner

SCAFFOLD FOR TISSUE REGENERATION IN MAMMALS

REFERENCE TO RELATED APPLICATION

This is a continuation of U.S. Ser. No. 12/504,489 filed Jul. 16, 2009 and issued Jul. 9, 2013 as U.S. Pat. No. 8,481,066.

FIELD OF THE INVENTION

This invention relates to a biocompatible scaffold for implantation into mammals to facilitate tissue repair, regeneration, and proliferation.

BACKGROUND OF THE INVENTION

Day et al. U.S. Pat. No. 6,709,744 describes bioactive materials for implantation which include borate-based glass or ceramic materials containing $Na_2O$—20 to 35 wt %
CaO—20 to 35 wt %
$P_2O_5$—0 to 10 wt %
$B_2O_3$—30 to 50 wt %

A specific example is a glass containing about 22.9 wt % $Na_2O$, about 22.9 wt % CaO, about 5.6 wt % $P_2O_5$, and about 48.6 wt % $B_2O_3$. These materials contain a high CaO concentration to facilitate the formation of hydroxyapatite when exposed to phosphorus-containing fluids in vivo or prior to implantation. These materials are in the form of loose particulates which are loosely packed, for example in a glass capillary tube for release into a host. Liang et al., Bioactive Borate Glass Scaffold for Bone Tissue Engineering, J. Non-Crystalline Solids 354 (2008), p. 1690-96; and Yao et al., In Vitro Bioactive Characteristics of Borate-Based Glasses with Controllable Degradation Behavior, J. Am. Cer. Soc. 90 (2007), p. 303-306 also disclose borate-based glasses formulated with high CaO to facilitate such formation of hydroxyapatite. For example, the 0B, 1B, 2B, and 3B glasses described by Yao et al. contain 0, 17.7, 35.4, and 53 wt. % borate.

SUMMARY OF THE INVENTION

Briefly, therefore, the invention is directed to a three-dimensional scaffold with interconnected pores for repair of tissue comprising a scaffold body for structural support of the tissue scaffold, where the scaffold body comprises scaffold body components bonded to each other to define the scaffold body and provide a scaffold body compressive strength of greater than 0.4 MPa, wherein the scaffold body components are of a component material comprising about 40 to about 90 wt % $B_2O_3$, and two or more other oxides from among those discussed hereinbelow, wherein the scaffold body has a porosity between about 15 and about 90 vol %.

Other objects and features of the invention are in part apparent and in part pointed out hereinafter.

DESCRIPTION OF PREFERRED EMBODIMENTS

Figure 1A:
FIG. 1A is a photograph of glass fibers employed in preparing a scaffold of the invention.

This is a continuation of U.S. Ser. No. 12/504,489 filed Jul. 16, 2009 and issued Jul. 9, 2013 as U.S. Pat. No. 8,481,066, the entire disclosure of which is incorporated by reference.

The tissue scaffold of the present invention in one aspect employs structural components in the form of one or more of fibers, hollow fibers, tubes, ribbons, solid spheres, hollow spheres, particles, and combinations thereof. The components are formed from a component material which is borate-based and which is glass, crystalline, or a combination of glass and crystalline, and which may or may not contain CaO for facilitating the formation of hydroxyapatite or other calcium phosphate compounds.

The structural scaffold body components are bonded to each other, typically by heating, to define the scaffold body and provide a scaffold body compressive strength of greater than 0.4 MPa. The desired compressive strength is selected so that the components are in no sense free flowing, and so that the scaffold body can be handled without disintegrating into the individual body components. The desired compressive strength is also selected to provide the strength that is required to remain integral after implantation, whether for repair of a load-bearing body part or non-load-bearing part, or one subject to impact or significant movement. In some preferred embodiments, the compressive strength of the scaffold body is at least about 5 MPa, while in other embodiments where greater rigidity is required, the compressive strength is at least about 20 MPa, such as between about 20 and about 200 MPa.

In a preferred embodiment the material contains the following, with all percentages herein being by weight, unless stated otherwise:

| | |
|---|---|
| $B_2O_3$ | 40 to 90 |
| $Na_2O$ | 0 to 25 |
| $Li_2O$ | 0 to 25 |
| $K_2O$ | 0 to 25 |
| $Rb_2O$ | 0 to 25 |
| CaO | 0 to 40 |
| MgO | 0 to 25 |
| SrO | 0 to 40 |
| BaO | 0 to 50 |
| $Li_2O + Na_2O + K_2O + Rb_2O$ | 0 to 50 cumulative |

| | | | | | | |
|---|---|---|---|---|---|---|
| MgO + SrO + BaO + CaO | | | | 0 to 50 cumulative | | |
| $P_2O_5$ | | | | 0 to 10 | | |
| $SiO_2$ | | | | 0 to 18 | | |
| $Al_2O_3$ | | | | 0 to 3 | | |
| F | | | | 0 to 4 | | |
| transition metal elements | | | | 0 to 10 cumulative. | | |

The concentrations of $K_2O$ and MgO in certain of these embodiments are each from about 1 to about 25 wt %. In most embodiments, the one or more of $Li_2O$, $Na_2O$, $K_2O$, and $Rb_2O$ is present in a cumulative concentration between about 1 and about 50 wt % and the one or more of MgO, SrO, BaO, and CaO is present in a cumulative concentration between about 1 and about 50 wt %, In most embodiments the scaffold consists only or essentially of components meeting these compositional requirements or other narrower descriptions herein. But generally speaking, for some embodiments other materials not meeting these descriptions may be incorporated into the scaffolds.

Exemplary scaffold component materials within this description contain, by weight %:

TABLE I

Wt. % Composition of Borate Glasses

| | $B_2O_3$ | $Na_2O$ | $K_2O$ | $Li_2O$ | CaO | BaO | MgO | $P_2O_5$ |
|---|---|---|---|---|---|---|---|---|
| A | 53 | 6 | 12 | | 20 | | 5 | 4 |
| B | 70.4 | | | 10.3 | 19.3 | | | |
| C | 63.8 | 19 | | | 17.2 | | | |
| D | 49.3 | 14.6 | | | | 36.1 | | |
| E | 78.5 | | | 11.5 | 10 | | | |
| F | 70 | | | 10.0 | 10.0 | 10.0 | | |
| G | 78.7 | | | 11.3 | | | 10.0 | |
| H | 78.7 | | | 11.3 | | 10.0 | | |
| I | 76 | | | 11 | 13 | | | |
| J | 59 | | | 8 | 33 | | | |

It can therefore be appreciated that the scaffolds include component materials containing 40 to 90 wt % $B_2O_3$ or 50 to 90 wt % $B_2O_3$, or even the narrower $B_2O_3$ ranges described herein, in combination with 1 to 25 wt % $Na_2O$, 1 to 25% $K_2O$, 1 to 40 wt % CaO, 1 to 25 wt % MgO, and 1 to 10 wt % $P_2O_5$. Or the component materials may contain 40 to 90 wt % $B_2O_3$, 1 to 25 wt % $Li_2O$, and 1 to 40 wt % CaO. Or they may contain 40 to 90 wt % $B_2O_3$, 1 to 25 wt % $Na_2O$, and 1 to 40 wt % CaO. Or they may contain 40 to 90 wt % $B_2O_3$, 1 to 25 wt % $Na_2O$, and 1 to 40 wt % BaO. Or they may contain 40 to 90 wt % $B_2O_3$, 1 to 25 wt % $Li_2O$, and 1 to 25 wt % MgO. Or they may contain 40 to 90 wt % $B_2O_3$, 1 to 25 wt % $Li_2O$, and 1 to 40 wt % BaO. While the scaffold component materials herein are described as containing various oxides by weight %, those skilled in the art understand that in the final glass or glass/crystalline composition, the individual oxygen, barium, boron etc. elements are largely dissociated, and the specific oxides, e.g., $B_2O_3$, are not separately identifiable or even necessarily separately present. Nonetheless, it is conventional in the art to refer to the final composition as containing a given % of the individual oxides, so that is done here. So from this perspective, the compositions herein are on an equivalent basis.

The scaffold component materials of the invention are borate-based in that they contain between about 40 and about 90 wt % $B_2O_3$, such as between about 50 and about 90 wt % $B_2O_3$. Borate glasses have several important advantages for biological use such as their ease of preparation, ability to be made into glass particulates, microspheres or fibers at relatively low temperatures without crystallization, and, particularly, their biocompatibility and high degree of bioactivity. The borate glasses disclosed herein, compared to silicate glasses, have significantly faster reaction rates, lower melting temperatures, resistance to crystallization, and in certain instances the absence of silica which only slowly degrades in the body. So while certain embodiments employ up to about 18 wt % $SiO_2$ in many other preferred embodiments herein, the scaffolds are silicate-free, containing less than 0.1 wt % silicate or even no silicate. Borate glasses form hollow fibers upon reaction in vivo, while silicate glasses do not; and they facilitate angiogenesis in vivo. The borate glasses described herein also release boron in-vivo as they react with the body fluids, and since boron has been reported to promote bone density, and to support the biological function of Mg and Ca, which are components of natural bone, borate glasses can provide an added function in bone repair/regeneration.

The self-bonded scaffolds of borate glass fibers, described in the examples and figures herein, reacted rapidly with body fluids such that they lose up to 60% of their initial weight and are completely impregnated with vascularized soft tissue in less than 4 weeks. The higher in vivo reaction rate of the borate glasses, which can be approximated by calculation as in below Example 9, substantially decreases the time the artificial material is in the body, and can promote faster complete healing of the defect. In preliminary in vivo experiments, borate glass appears to produce a significantly milder immune response than commercial bioactive silicate glass compositions.

There is one embodiment which has specific preference in certain applications and wherein the concentration of Ca (elemental or in CaO or other compounds) in the scaffold body component material is controlled to less than about 5 wt %. Certain preferred embodiments strictly control the Ca concentration to less than about 0.5 wt %, such as to less than 0.2 wt %, and even to less than 0.1 wt %. The advantage in this embodiment to strictly controlling Ca concentration is the avoidance of the formation of apatite and related compounds upon exposure to physiological phosphorus-containing fluids. Such apatite compounds include hydroxyapatite $Ca_5(PO_4)_3(OH)$, fluoroapatite $Ca_5(PO_4)_3F$, and amorphous calcium phosphate (ACP). In certain applications it is advantageous to avoid the formation of Ca-apatite compounds because they have a relatively lower radiopacity than do, for example, analogous Ba compounds. In certain situations it is advantageous to avoid Ca-apatite compounds in order to form compounds which degrade more rapidly, or perhaps even more slowly. It can also be advantageous to avoid Ca for purposes of controlling melt characteristics, such as viscosity, melting temperature, and/or crystallization tendency.

The scaffold of the invention which is constructed from Ca-free material in one embodiment preferably contains between about 40 and about 90 wt % $B_2O_3$ with the remainder being selected from alkali oxides and alkaline earth oxides, and other optional constituents listed below. For example, this scaffold material contains, by weight %:

| | |
|---|---|
| $B_2O_3$ | 40 to 90 |
| $Na_2O$ | 0 to 25 |
| $Li_2O$ | 0 to 25 |

-continued

| | |
|---|---|
| $K_2O$ | 0 to 25 |
| $Rb_2O$ | 0 to 25 |
| MgO | 0 to 25 |
| SrO | 0 to 40 |
| BaO | 0 to 25 |
| $Li_2O + Na_2O + K_2O + Rb_2O$ | 0 to 50 cumulative |
| MgO + SrO + BaO | 0 to 50 cumulative |
| $P_2O_5$ | 0 to 10 |
| $SiO_2$ | 0 to 18 |
| $Al_2O_3$ | 0 to 3 |
| F | 0 to 4 |
| transition metal elements | 0 to 10 cumulative. |

Certain of these embodiments contain low levels of Ca, as described above; while others are substantially Ca-free and contain essentially no or less than 0.1 wt % Ca.

In one preferred embodiment, the material contains between about 50 and about 80 wt % $B_2O_3$; between about 5 and about 20 wt % alkali oxide component selected from the group consisting of $Li_2O$, $Na_2O$, $K_2O$, $Rb_2O$, and combinations thereof; and between about 5 and about 40% alkaline earth component selected from the group consisting of MgO, SrO, BaO, and combinations thereof. While $P_2O_5$, $SiO_2$, $Al_2O_3$, F, and transition metal elements. Lanthanides are specifically and strictly excluded from certain preferred embodiments. In some embodiments the scaffold material consists essentially of between about 50 and about 80 wt % $B_2O_3$; between about 5 and about 20 wt % alkali oxide component selected from the group consisting of $Li_2O$, $Na_2O$, $K_2O$, $Rb_2O$, and combinations thereof; and between about 5 and about 40 wt % alkaline earth component selected from the group consisting of MgO, SrO, BaO, and combinations thereof.

Exemplary borate-based scaffold component Ca-free materials contain, by weight %:

TABLE II

Wt. % Composition of Ca-Free Borate Glasses

| | $B_2O_3$ | $Na_2O$ | $Li_2O$ | MgO | BaO |
|---|---|---|---|---|---|
| I | 49.3 | 14.6 | | | 36.1 |
| II | 78.7 | | 11.3 | 10 | |
| III | 78.7 | | 11.3 | | 10 |
| IV | 76 | | 11 | | 13 |
| V | 59 | | 8 | | 33 |
| VI | 45 | | 7 | | 48 |
| VII | 70 | | 10 | 10 | 10 |

In certain embodiments of the invention, the scaffold component materials are selected to include at least two of the alkali oxides $Li_2O$, $Na_2O$, $K_2O$, and/or $Rb_2O$ in a cumulative concentration of between about 5 and about 25 wt %, such as between about 8 and 20 wt %. It has been discovered to be advantageous to include two or more such alkali compounds in order to reduce the tendency for crystallization, which ultimately improves the workability and manufacturability of the glasses to make scaffolds. Using more than one type of alkali (i.e., mixed alkali) can reduce the cost of a glass, modify its reaction rate with body fluids, and provide additional elements beneficial to bone growth and regeneration.

A further feature of certain embodiments of the invention is that the cumulative concentration of the alkaline earth oxides from the group consisting of MgO, SrO, BaO, CaO, and combinations thereof is in the range of 1 to about 50 wt %, such as in the range of 1 to 30 wt %, or even about 8 to 25 wt %. Certain of these embodiments contain two or more such alkaline earth oxides in a range of 1 to 45 wt % cumulatively, such as in the range of 5 to 25 wt %.

These scaffold embodiments employing scaffold material with mixed alkali oxide contents contain $B_2O_3$ from about 40 to about 90 wt %. Certain of these embodiments consist essentially of $B_2O_3$ from about 40 to about 90 wt %, mixed alkali oxides selected from the group consisting of $Li_2O$, $Na_2O$, $K_2O$, and $Rb_2O$, and one of MgO, SrO, BaO, or CaO. Other embodiments consist essentially of $B_2O_3$ from about 40 to about 90 wt %, two or more alkali oxides selected from the group consisting of $Li_2O$, $Na_2O$, $K_2O$, and $Rb_2O$, and two or more alkaline earth oxides from the group consisting of MgO, SrO, BaO, and CaO. For example, composition A in Table I consists essentially of $B_2O_3$ from about 40 to about 90 wt %, two or more mixed alkali oxides selected from the group consisting of $Li_2O$, $Na_2O$, $K_2O$, and $Rb_2O$ in a cumulative wt % between 5 and 25%, and two or more from among MgO, SrO, BaO, and CaO in a cumulative wt % between 8 and 25%. Other embodiments optionally include one or more of $P_2O_5$, $SiO_2$, $Al_2O_3$, F, and transition metal elements.

The invention includes scaffold embodiments employing scaffold material with an especially high $B_2O_3$ composition, namely, from about 60 to about 90 wt %, preferably from about 60 to about 82 wt %, still more preferably from about 70 to about 80 wt %. These embodiments employ an alkali oxide selected from the group consisting of $Li_2O$, $Na_2O$, $K_2O$, $Rb_2O$, and combinations thereof cumulatively from about 1 to about 50 wt %, such as from about 5 to about 25 wt %, and even from about 8 to about 20 wt %; and even optionally two or more such oxides cumulatively in this range. They also optionally employ alkaline earth oxides from group consisting of MgO, SrO, BaO, CaO, and combinations thereof in the range of about 1 to about 50 wt %, such as in the range of 1 to 30 wt %, or even about 8 to 25 wt %, and even two or more such oxides cumulatively in this range. Certain of these embodiments consist essentially of these components, such as compositions II, III, IV, and VII in Table II; while other embodiments optionally include one or more of $P_2O_5$, $SiO_2$, $Al_2O_3$, F, and transition metal elements.

In the foregoing described mixed-alkali and high-borate embodiments, the Ca concentration may be strictly controlled to less than about 5 wt %, including to less than 0.5 wt %, such as to less than 0.2 wt % or less than 0.1 wt % to avoid the formation of Ca compounds. Alternatively, there are embodiments containing two or more alkali oxides which also contain CaO in an amount up to about 40 wt % to facilitate the formation of hydroxyapatite, other calcium phosphate compounds, or amorphous calcium phosphate.

Another specific embodiment of the invention contains one or more elements selected from the group consisting of Zn, Cu, Fe, Mn, Si, F, Sr, Ni, Mo, and Se, in an amount between about 0.01 and 10 wt % per element and cumulatively less than 25 wt %. These are provided to the glass in the form of oxides or other compounds. These various optional elemental additions provide specific functions and advantages for specific applications. One or more of these elements within these ranges may also optionally be included in the previously described embodiments, i.e., the embodiment in which the cumulative concentration of the various alkali oxides from the group consisting of $Li_2O$, $Na_2O$, $K_2O$, $Rb_2O$, and combinations thereof is maintained in the range of about 0 to about 30 wt %, and the embodiment in which the Ca concentration is strictly controlled to less than about 0.2 wt %, such as to less than 0.1 wt %. The trace elements may be incorporated as oxides into the scaffold materials.

Nickel increases endothelial cell motility, which is an important step to angiogenesis. Cell motility is the migration of cells due to a stimulant, in this case the presence of the trace element Ni.

Selenium functions as an antioxidant that is capable of protecting the body against oxidative stress associated with the natural immune response of creating excess reactive oxygen species to kill and destroy microbial pathogens and viruses. Essentially, the selenium is keeping the reactive oxygen species in check so that there is no negative response to the body cells and tissues. Animals with deficiencies in selenium have shown impaired immune responses that resulted in phagocytic neutrophils and macrophages unable to combat antigens. Selenium supplementation in animal models has been shown to increase several immune functions, including, but not limited to; neutrophil migration, T-cell proliferation and function, cytotoxic T-cell activity, T-cell response, lymphokine-activated killer cell activity, and vaccine-induced immunity to malaria and polio. Most of these immune functions are natural to the wound healing process and increasing or promoting these cellular activities would promote wound healing. Therefore incorporating Se in the components of the invention promotes and stimulates natural biological immune responses required for soft tissue healing and regeneration.

Zinc is a cofactor required for the formation of alkaline phosphatase, an enzyme found in bone tissue. The greatest amount of Zn in bone is located in the layer of osteoid prior to calcification. Zinc is a cofactor with Mg, therefore both must be present to gain the benefits of either. Zinc has been found to incorporate into hydroxyapatite, and when F is also present, the Zn and Zn—F complex may improve the crystallinity of the apatite.

Copper, when deficient, inhibits bone growth and increases the changes associated with osteoporosis. Copper does not become incorporated into the HA, but is used by the osteoblast and osteoclast cells. When there is a deficiency, both osteoblast (bone formers) and osteoclast (bone resorbers) decrease in activity. Osteoporosis is triggered by the greater relative reduction of osteoblast compared to the osteoclast. Copper has also been shown to have an effect on endothelial cell migration which can be useful for blood vessel formation and has potential importance for both hard and soft tissue regeneration. The source of Cu to the glass may be a copper oxide such as CuO or $Cu_2O$ or other copper compounds such as copper nitrate or copper sulfate, for example. In one embodiment the copper compound is incorporated into the glass in a concentration of between about 0.05 and about 5 wt %, such as between about 0.1 and about 2.5 wt %. There are preferred embodiments employing from about 1 wt % to about 2 wt % copper compound, such as from about 1 wt % to about 2 wt % CuO.

Iron acts as a signal for the enzymes that produce collagen. Removal or absence of Fe will basically turn off the enzymes.

Manganese acts as a cofactor for glycosyltransferases, which is the transfer of sugar from a nucleotide-diphosphate sugar to an acceptor molecule. Manganese is essential for several formation stages of glycosaminoglycan chondroitin sulphate. Chondroitin sulphate is a major constituent in connective tissues such as blood vessels, bone, and cartilage.

Silicon is essential for normal bone matrix formation and possibly bone mineralization. Deficiencies of Si can cause conditions of depressed growth, abnormalities associated with the skull, long bone, and overall bone architecture. Silicon in bone is primarily located in osteoblast mitochondria, the cells responsible for forming new connective tissue matrix material.

Fluorine can affect hydroxyapatite crystallization by replacing a hydroxyl ion and improving the stability of the crystals. It is important to note that F must be incorporated into bone as it is forming, because it will not diffuse into formed bone. The skeletal system responds to F by increasing the number of osteoblast (bone forming cells), hence forming more bone. The increase in osteocytes is due to the F increasing osteoprogenitor cell proliferation by increasing the activity of the bone cell mitogens (proteins that promote cell division).

Strontium is believed to have metabolic effects on bone formation. Strontium has been shown in several animal models to reduce osteoclast (bone resorbing cells) activity without any toxic effect on the osteoclast cells. Increased replication of pre-osteoblastic cells has been seen with addition of Sr and led to an increase in bone matrix synthesis. Strontium has been considered as a component for future treatment of osteoporosis.

Accordingly, some exemplary scaffolds of the invention such as in below Example 7 are constructed from scaffold body components such as fibers which contain, approximately, 40 to 90 wt % $B_2O_3$, 0.1 to 5% CuO, and $Na_2O$, $K_2O$, MgO, and $P_2O_5$. More specific examples contain or even consist essentially of 40 to 90 wt % $B_2O_3$, 0.1 to 5% CuO, 1 to 25 wt % $Na_2O$, 1 to 25 wt % $K_2O$, 1 to 25 wt % MgO, and 1 to 10 wt % $P_2O_5$.

The scaffold component material may be glassy, glass ceramic, or ceramic in nature. However the glassy state is preferred in this invention because, generally speaking, glassy materials are stronger and more chemically homogeneous than their crystalline or partially crystalline counterparts of the same composition. It is therefore preferable that the scaffold body component material is substantially glass in that less than about 5 wt %, more preferable less than 1 wt %, of the component material is crystalline material. More particularly, it is preferable that there is less than 5 wt %, preferably less than 1 wt %, crystallization when the material is heated to 800 C at an average heating rate of 20 C/min, held at that temperature for 10 minutes, then cooled to room temperature by exposure to STP conditions of room temperature and atmospheric pressure. More preferably, the glass will contain less than 5 wt % crystallization, even more preferably less than 1 wt % crystallization, after being heated to 575 C with a ramp rate of 20 C/min, and held at that temperature for 20 minutes, then cooled to room temperature by exposure to STP conditions.

The scaffold body components of the invention are in the form of solid fibers, hollow fibers, ribbons, solid spheres, hollow spheres, particles, and combinations thereof. In an especially preferred embodiment for many applications, the scaffold body components include fibers, and in certain such embodiments the scaffold body consists essentially of components which are fibers. The fibers have an aspect ratio of at least 2:1 length:transverse dimension (e.g., diameter), and more typically at least 5:1, such as greater than 10:1. In certain embodiments of the invention, the scaffold body components are primarily one form, such as fibers, in combination with a minor constituent of a second form from the foregoing options, such as microspheres.

There is also an option with this invention of employing distinct component compositions to strategically impart certain properties. For example, the scaffold body employs 10 to 90 wt % of components having a composition selected from the above Tables I and II, and 10 to 90 wt % of components of a different composition from these Tables. Or even more than two such types of components may be employed. That is, the scaffold may contain at least 10 wt % of the scaffold body components comprising a first component material within the contemplated compositions and at least 10 wt % of scaffold body components comprising a second component material within the contemplated compositions, wherein the first and second component materials have compositions distinct from each other. This permits the selection of, for example, faster reacting fibers in combination with slower reacting fibers; or the selection of Ca-containing fibers with Ca-free fibers; or the selection of trace element-containing fibers with non-trace-element-containing fibers, to name a few combinations. One can therefore select standard composition components and combine them with non-standard composition components to effectively customize or dope the scaffold for the application presented, or for the host's particular needs. Alternatively, hollow spheres containing a growth factor or drug for delivery to the host can be incorporated with other structural components, such as fibers.

The scaffold is formed to have a porosity which is selected to provide fluid flow into the scaffold to facilitate uptake of bodily fluids, while maintaining sufficient strength for handling and implantation. The porosity is between about 15 vol % and about 90 vol %. There are different levels of porosity, for example between about 15 and about 30 vol %, or between about 30 and about 60 vol %, or between about 60 and about 90%, which are preferred for different applications. Porosity depends on or is controlled by many factors such as fiber orientation, shape of particles or microspheres, and the thermal treatment (time/temperature) used to bond the elements together. Independent of this bulk porosity, interconnectivity is also important in the scaffolds of the invention. Because tissue repair is strongly influenced by flow of bodily fluids into the scaffold, it is preferred to have a high level of interconnectivity of pores within the scaffold, and a low level of closed pores. That is, it is important that most pores be connected to other pores, and that there is a direct or indirect path from most pores to the exterior surface of the scaffold. In certain embodiments, at least about 80 vol %, such as at least about 90%, of the pore volume of the scaffold is directly or indirectly through other pores accessible from the scaffold exterior, and therefore accessible to bodily fluids.

The method of making the scaffold component materials is not critical to the invention. By way of example, in preparing the scaffold component materials, individual analytical reagent grade components are weighed, mixed thoroughly, and melted in a platinum crucible for approximately one hour at 1050 C. The melt is then quenched, for example, on a steel or copper plate to form glass that can be ground into particulates of a desired size. The particulates can be spheroidized to form microspheres of a chosen diameter. The material of preferred composition when in the form of a melt can easily be formed into fibers. If fibers of the borate glass are made, they can either be pulled by hand directly from the melt or pulled through bushing by a rotating drum.

The components can be self bonded to form three dimensional scaffolds by simply heating an assemblage of particulates in a furnace and allowing the fibers/particles/spheres to soften and bond to each other. After the allotted time at temperature, the construct is removed from the furnace and cooled to room temperature. Many prior bioactive glasses, such as 45S5, are difficult to self bond due to crystallization of the glass. Therefore the self-bonding ability of the borate glasses of the invention is a distinct advantage over other bioactive materials currently in use.

EXAMPLE 1

Figure 1B:
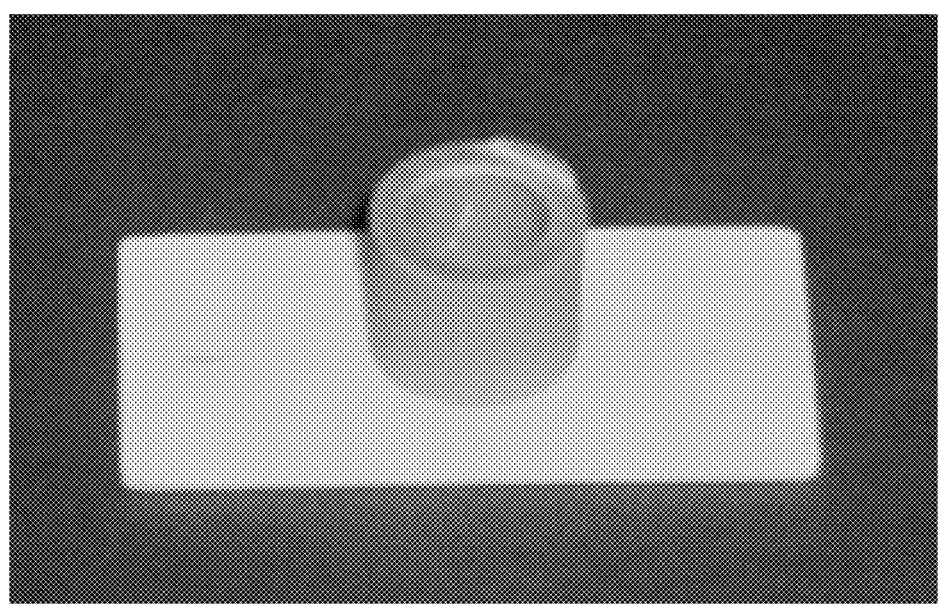
FIG. 1B is a photograph of a mold used in preparing a scaffold of the invention.
Figure 1C:
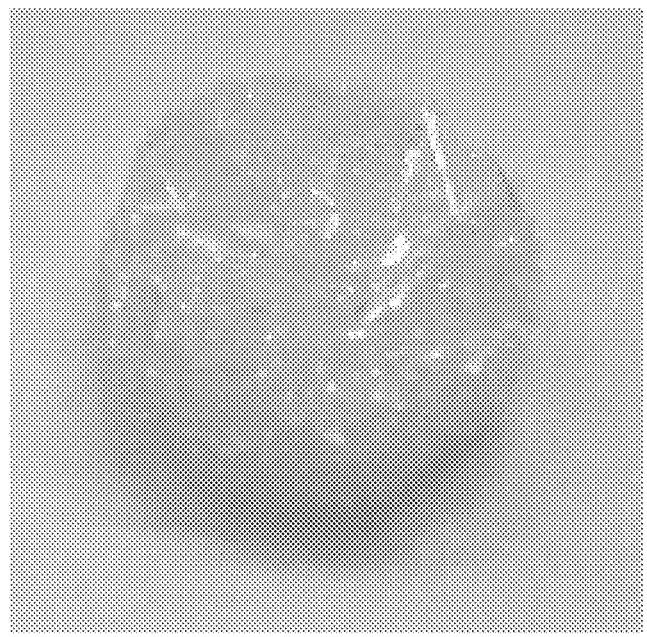
FIG. 1C is a photograph of a scaffold of the invention.

A scaffold of the invention was formed from glass fibers shown in FIG. 1A, which were about 3 mm long on average and between about 100 and about 300 microns in diameter. The fiber composition was, by wt %, 53 $B_2O_3$, 6 $Na_2O$, 12 $K_2O$, 5 MgO, 20 CaO, and 4 $P_2O_5$. The fibers were placed in the scaffold mold (mullite tube) of FIG. 1B, which was 7 mm in diameter, and enough fiber was placed in the mold (70 mg) to make a scaffold 2 mm in height. The mold with fibers randomly oriented therein was placed in a furnace, with an atmosphere of air and ambient pressure, and heated for 45 minutes at 575 C. The temperature ramp rate to 575 was about 100 C/min. The scaffold was then removed from the furnace and the mold allowed to air cool at room temperature. The scaffold was then removed from the mold and is depicted in FIG. 1C.

EXAMPLE 2

Figure 2:
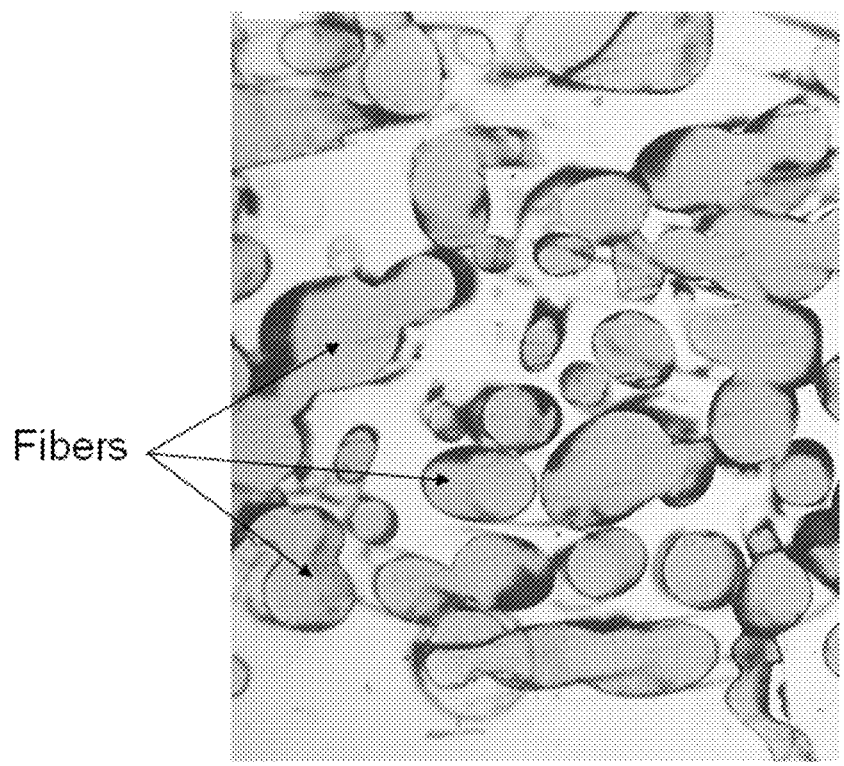
FIG. 2 is a photograph of a cross section of a scaffold of the invention.

A borate based glass fiber scaffold of the invention was prepared in the manner described in Example 1 and embedded in epoxy. A cross section was formed and an optical photomicrograph was taken and is shown in FIG. 2. The lighter areas are the epoxy, while darker, rounded shapes are the glass fibers. They have irregular shapes due to the random orientation of the fibers in the scaffold. Substantial self bonding is evident where two or more rounded shapes joined. The high degree of interconnectivity of porosity is also evident from this figure.

EXAMPLE 3

Figure 11:
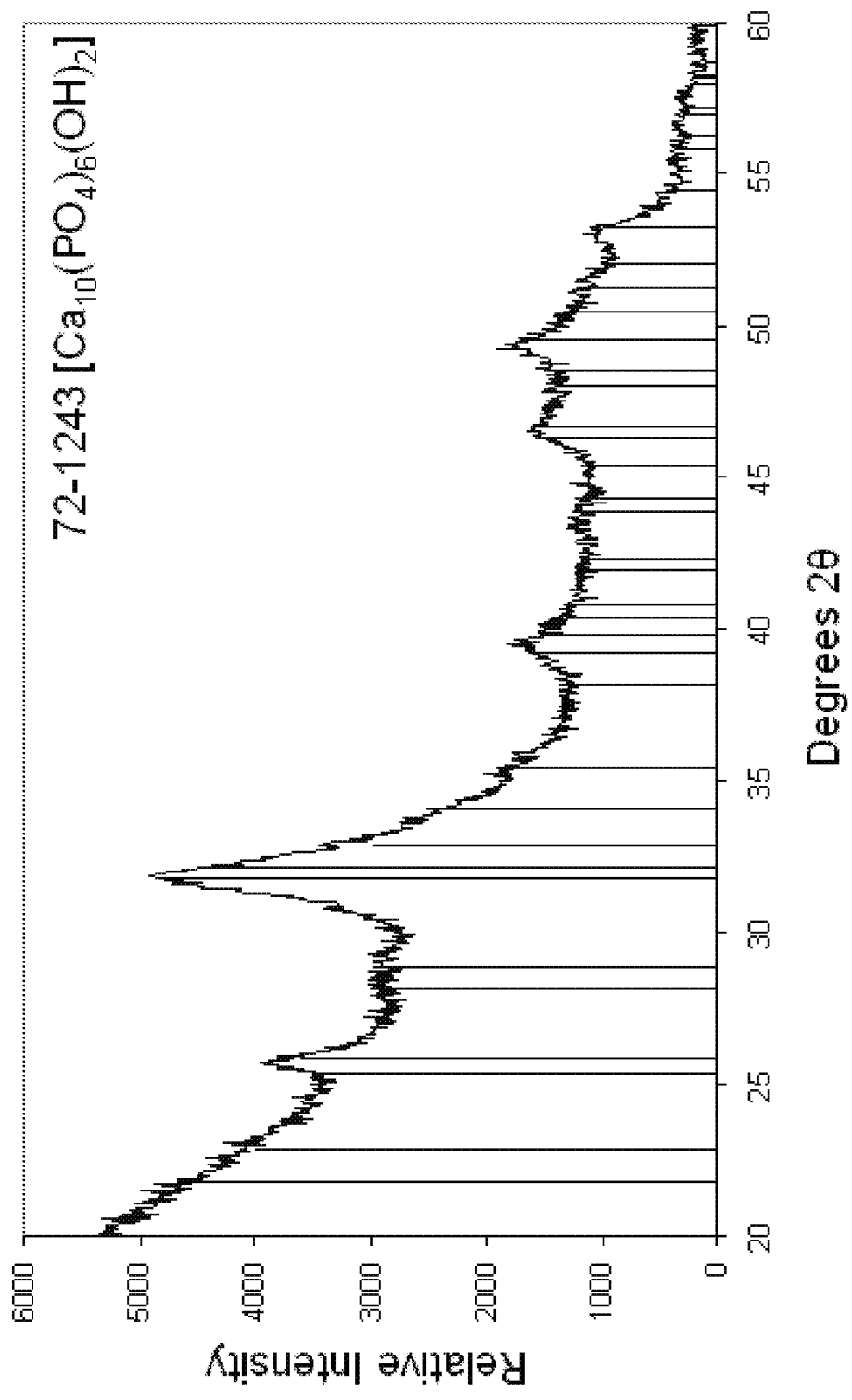
FIG. 11 is an x-ray diffraction profile of a scaffold discussed in a below Example.
Figure 12A:
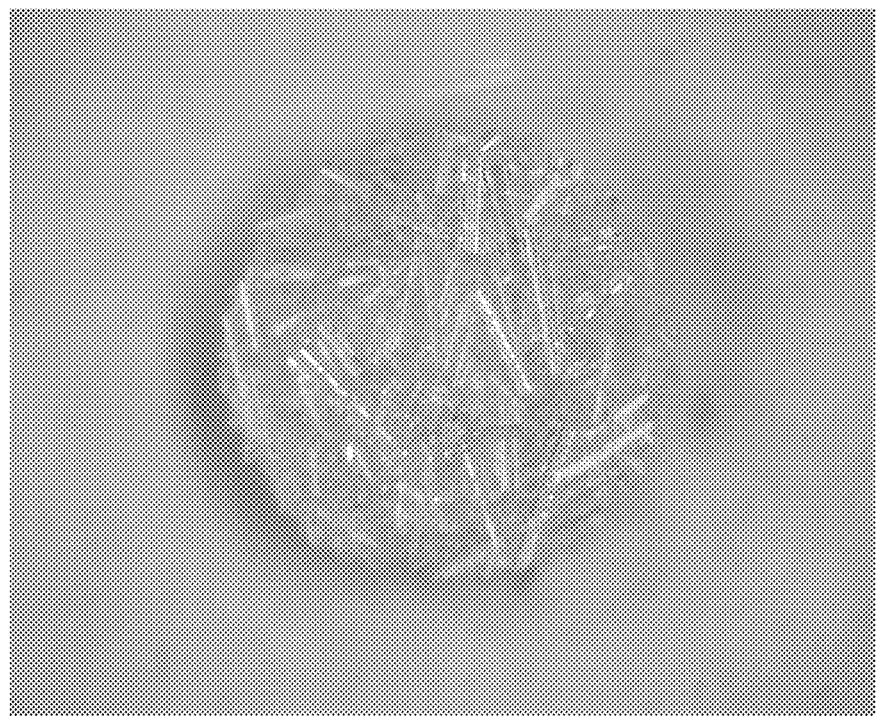
FIGS. 12A, 12B, 12C, 12D, 12E, and 12F are photographs of scaffolds according to an Example.
Figure 12B:
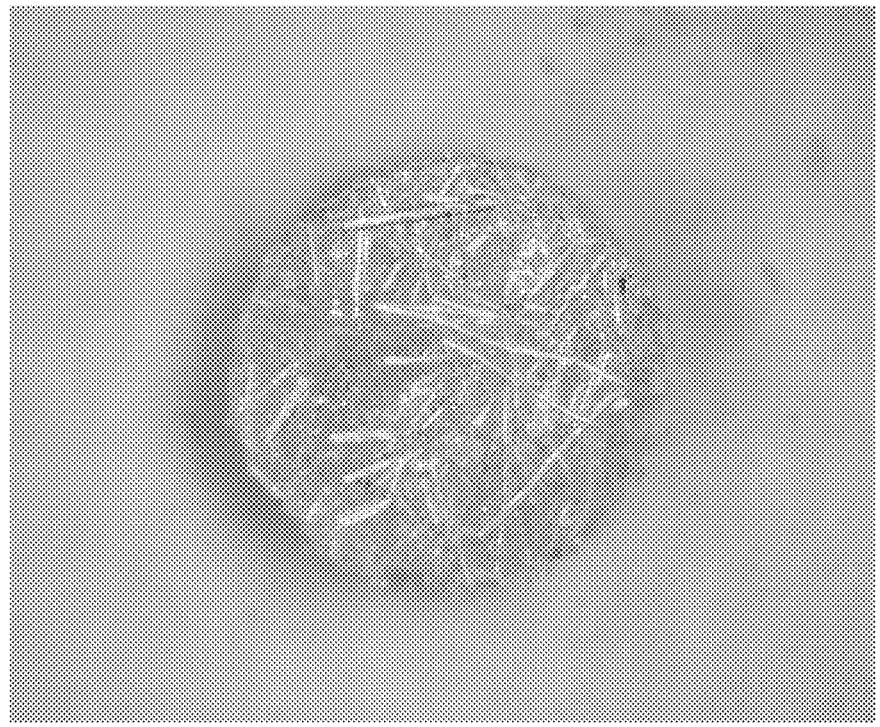
Figure 12C:
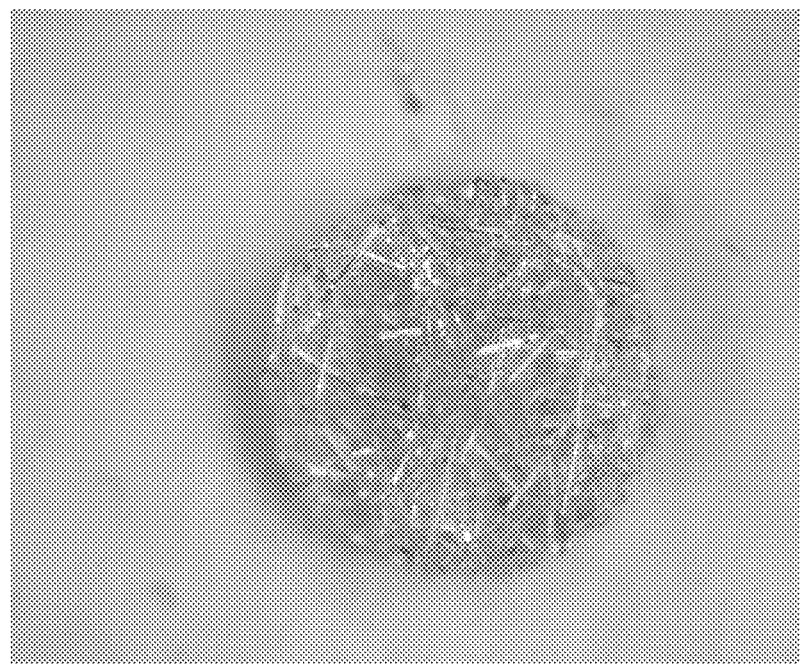
Figure 12D:
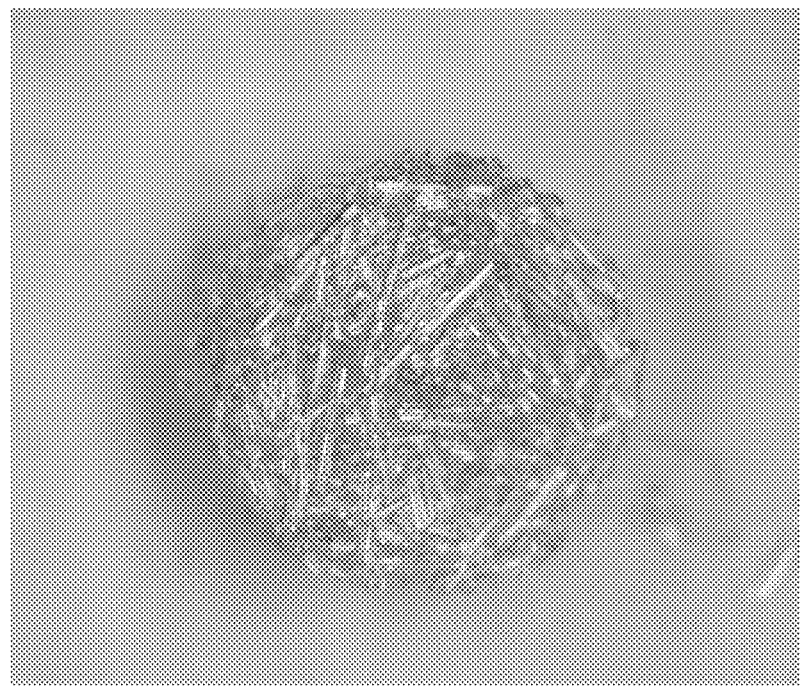
Figure 12E:
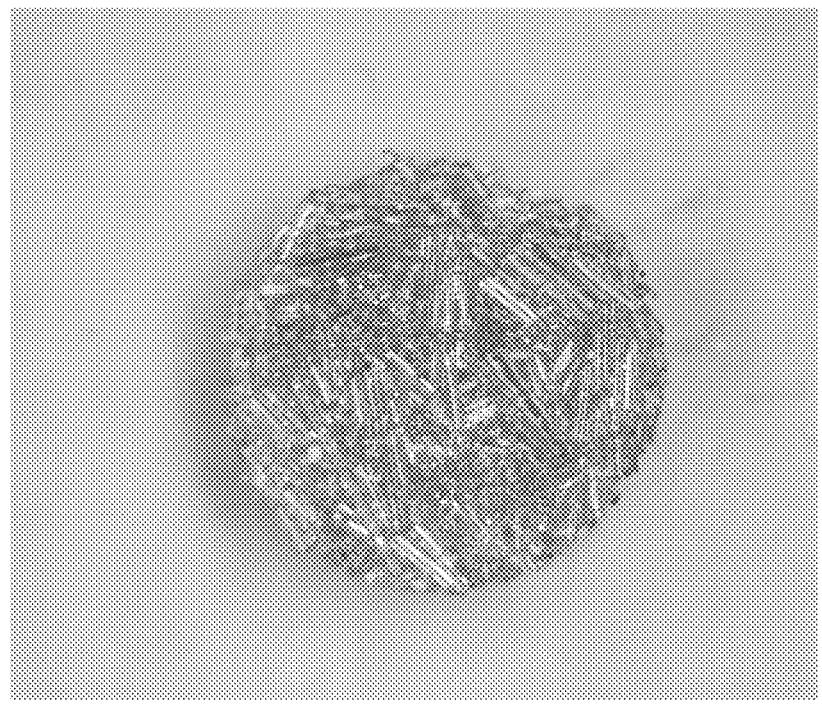
Figure 12F:
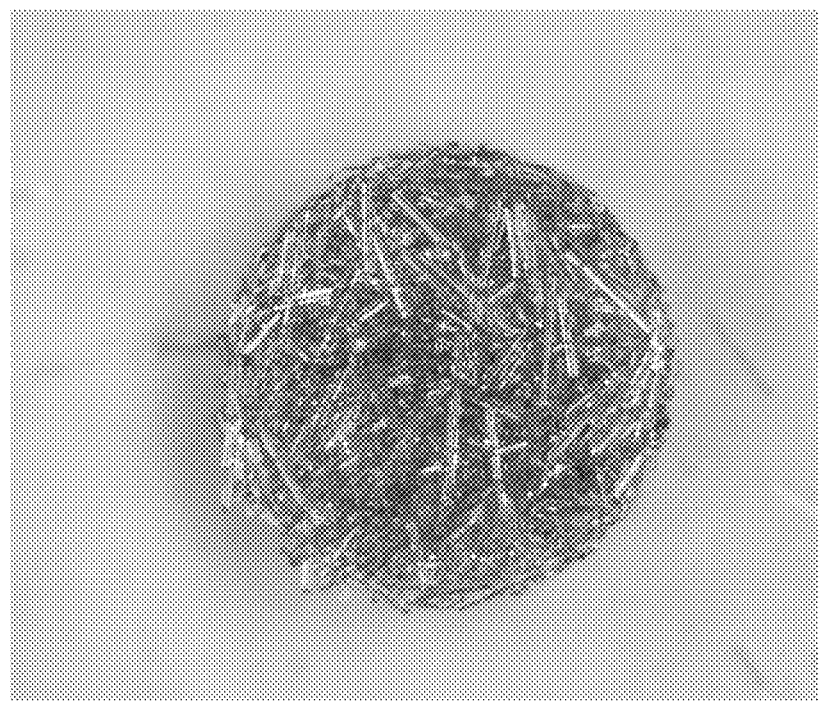
Figure 13A:
FIGS. 13A, 13B, 13C, 13D, 13E, 13F, 14A, 14B, 14C, 14D, 14E, and 14F are photographs of scaffolds of FIGS. 12A, 12B, 12C, 12D, 12E, and 12F after implantation.
Figure 13B:
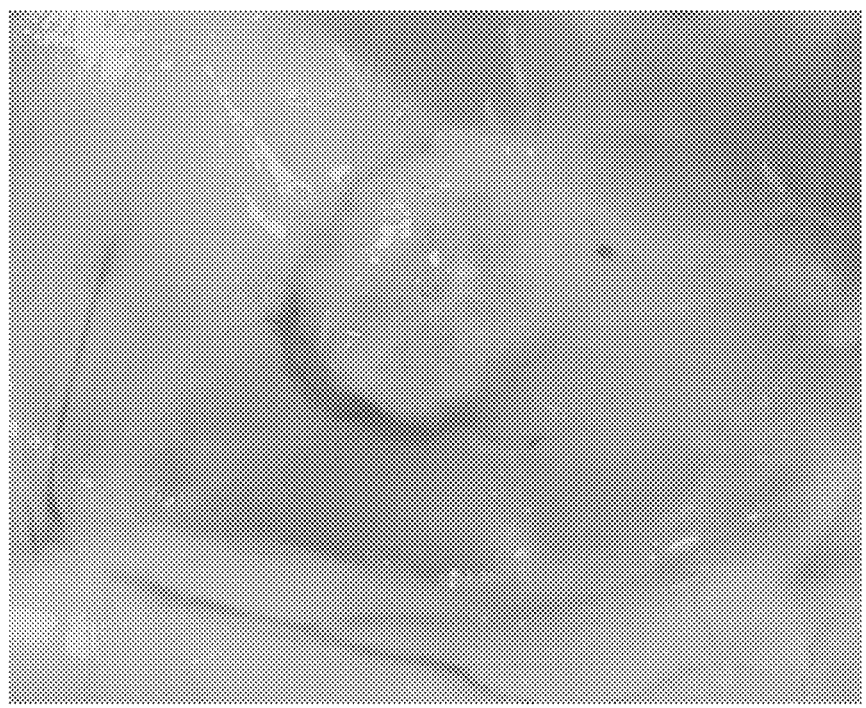
Figure 13C:
Figure 13D:
Figure 13E:
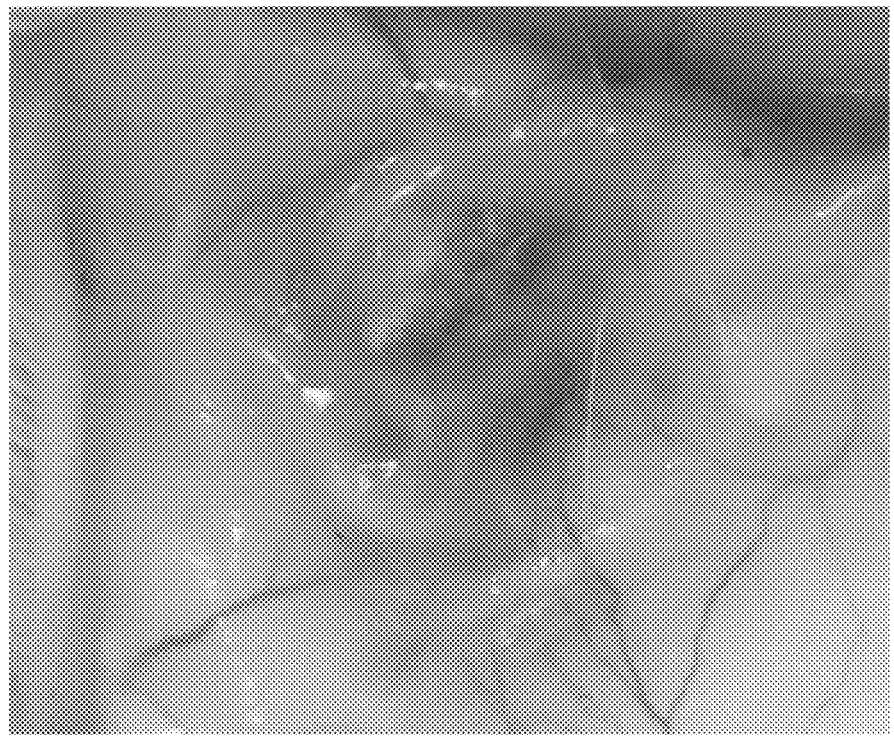
Figure 13F:
Figure 14A:
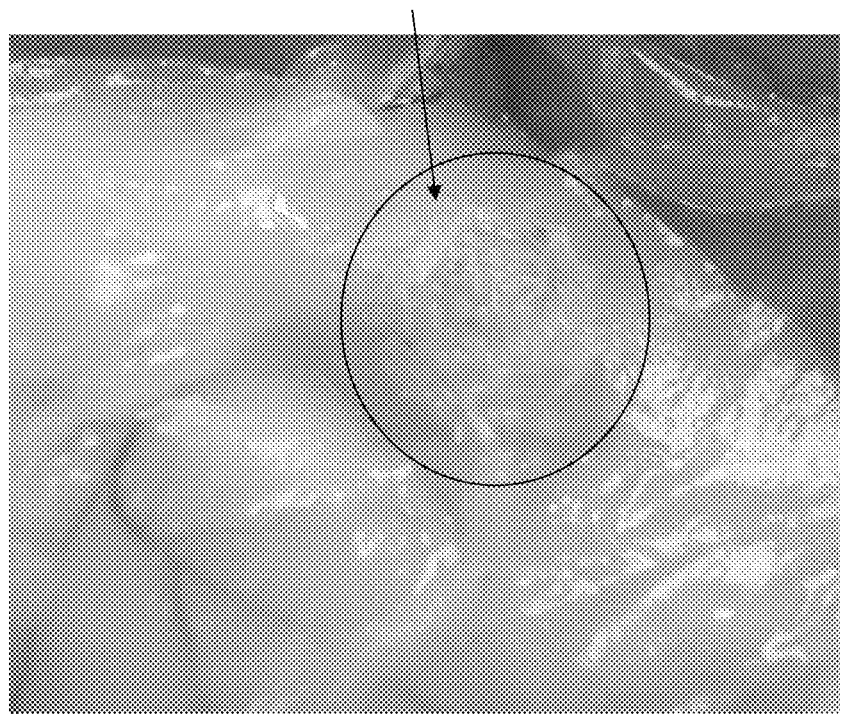
Figure 14B:
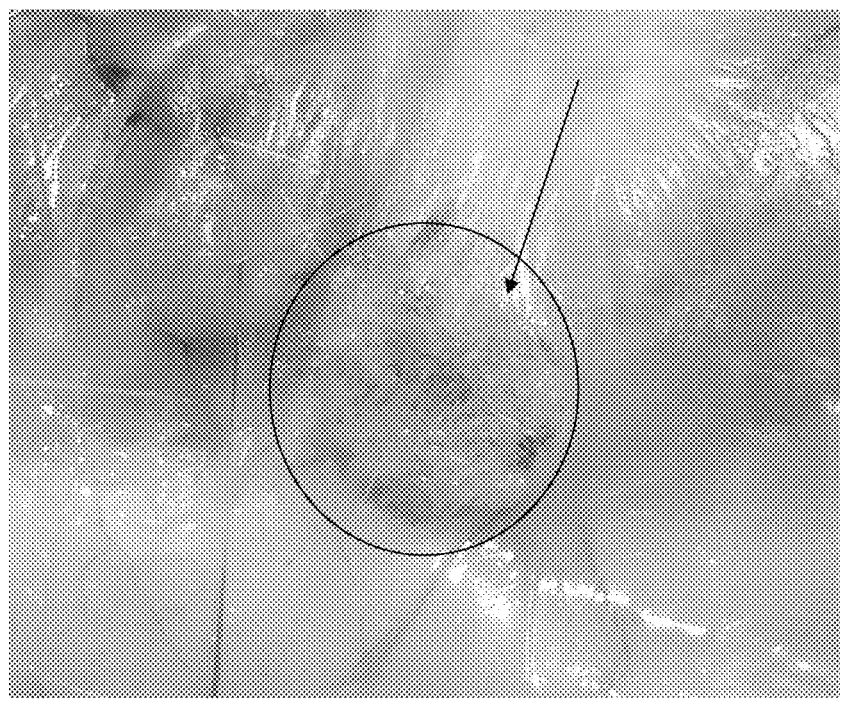
Figure 14C:
Figure 14D:
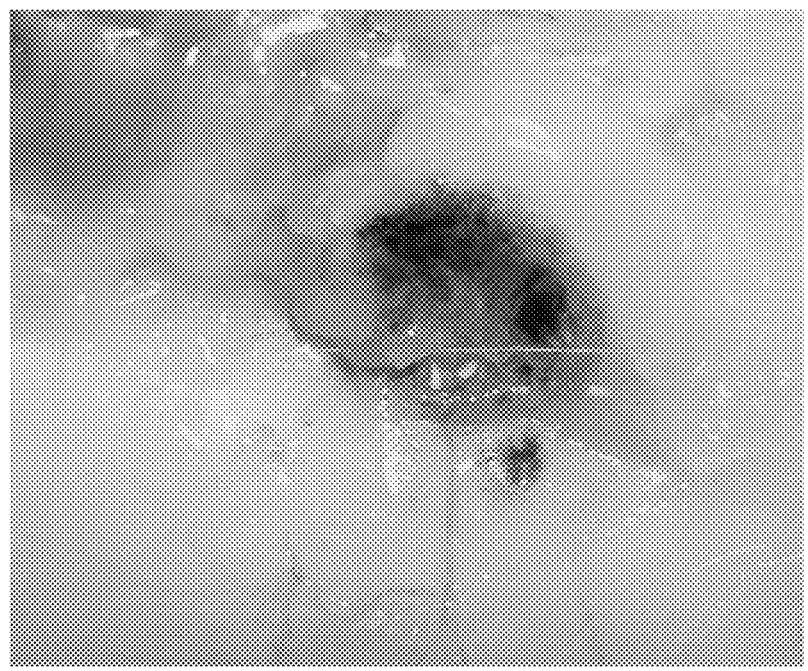
Figure 14E:
Figure 14F:
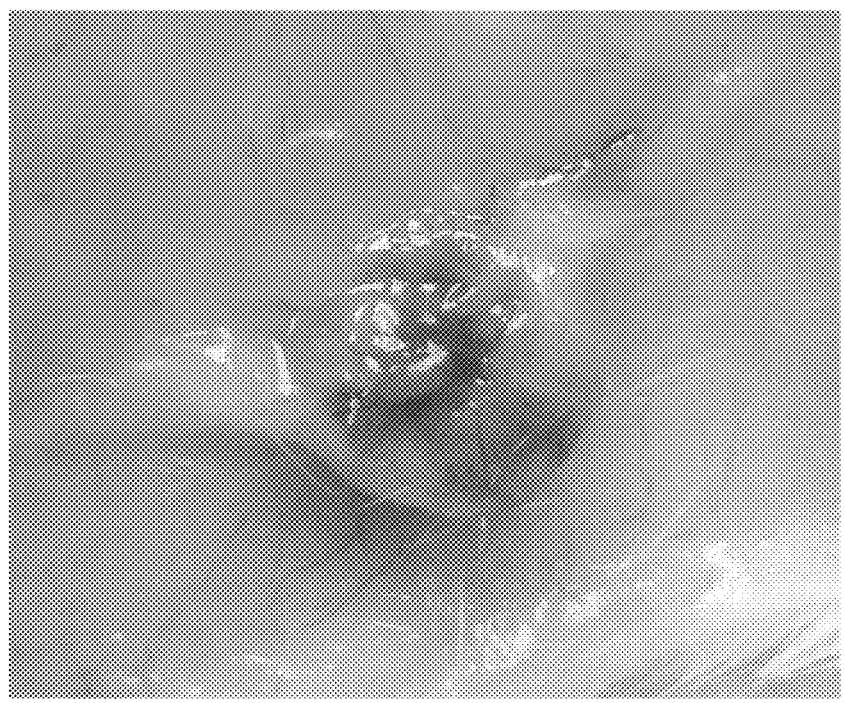

A self-bonded borate glass scaffold of the type of Examples 1 and 2 was implanted subcutaneously in the back of a rat. After four weeks, the scaffold was removed and examined by scanning electron microscopy (SEM). A micrograph was taken (FIGS. 3A and 3B) which revealed soft tissue surrounding the fibers. This demonstrates uptake of physiological fluid into the scaffold and growth of soft tissue within the scaffold. A hollow core formed in many of the fibers, as shown, indicating reaction of the glass fibers with physiological fluids. This is in contrast to the solid nature of the fibers prior to implantation as shown in FIG. 2. FIGS. 4A, 4B, 4C, and 4D are micrographs at successively higher magnifications of one of the fibers from FIGS. 3A and 3B. The porous reaction layer visible in FIGS. 4C and 4D is evidence of hydroxyapatite formation. This is confirmed by the x-ray diffraction analysis of the scaffold shown in FIG. 11, which reveals a pattern consistent with $Ca_{10}(PO_4)_6(OH)_2$.

EXAMPLE 4

Figure 3A:
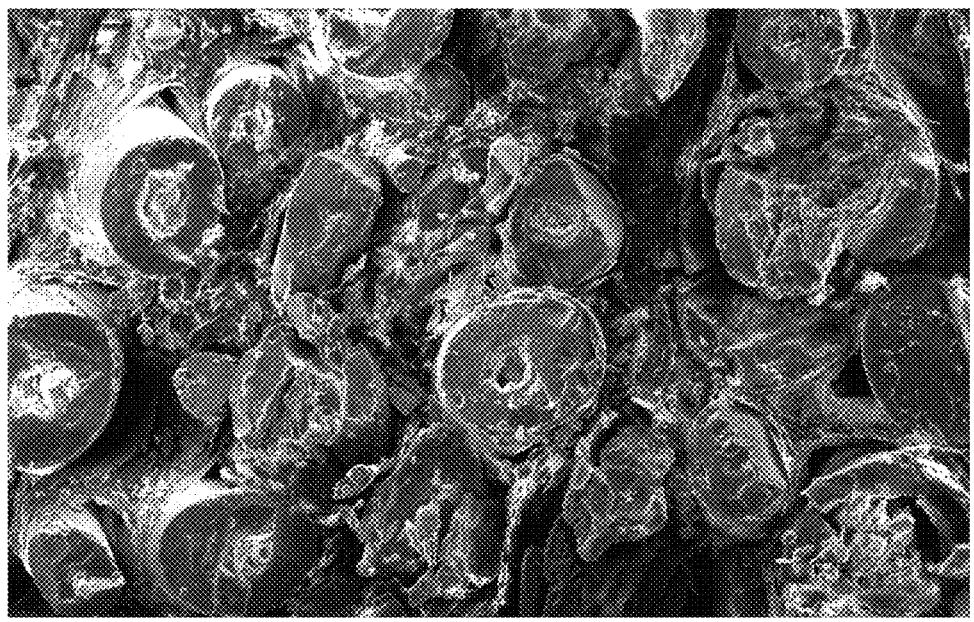
FIGS. 3A, 3B, 4A, 4B, 4C, and 4D are SEM micrographs of cross sections of a scaffold of the invention.
Figure 3B:
Figure 4A:
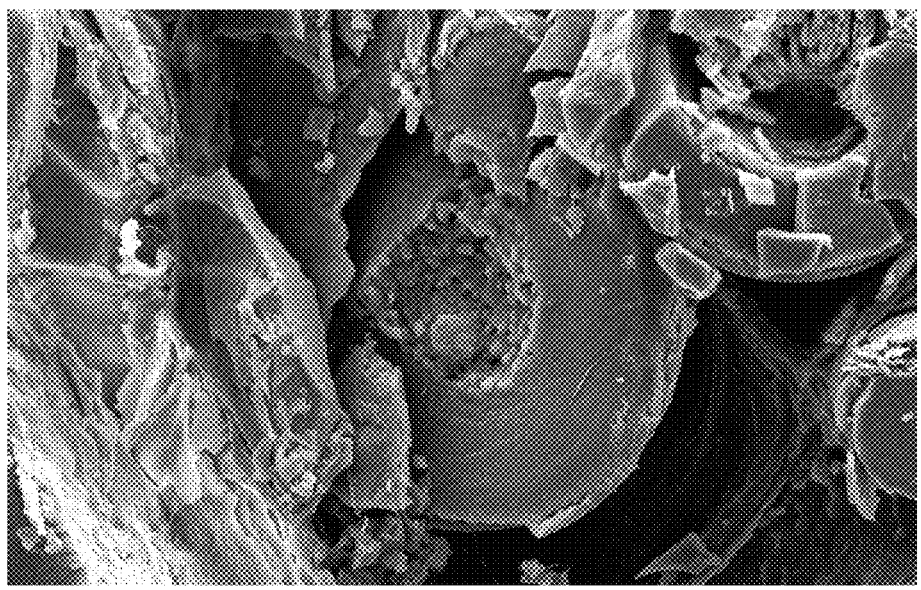
Figure 4B:
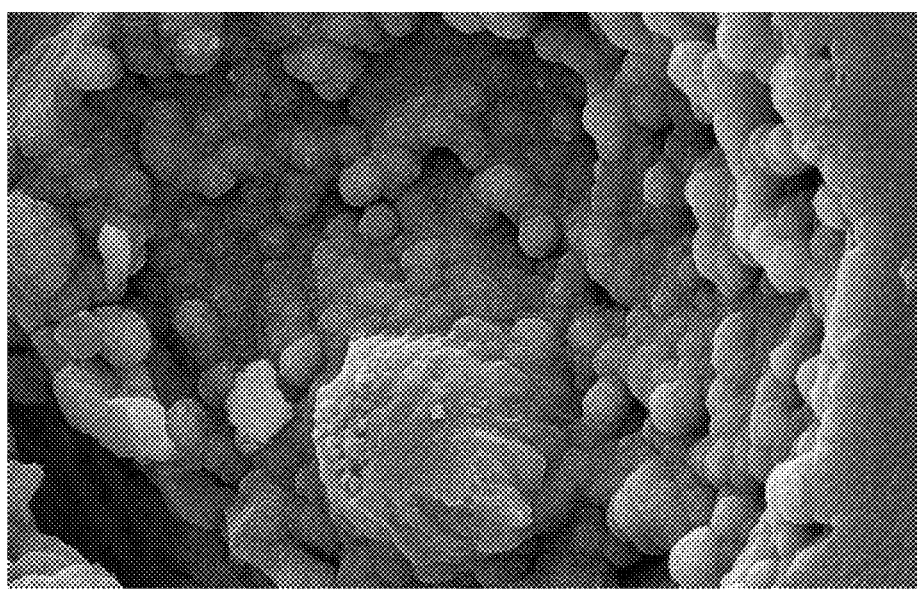
Figure 4C:
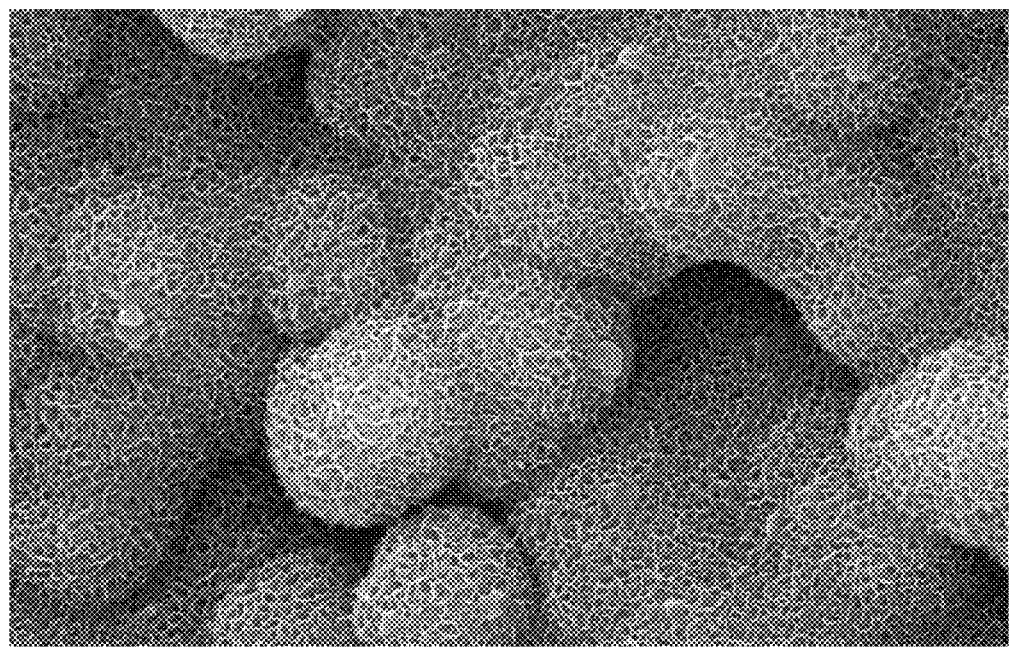
Figure 4D:
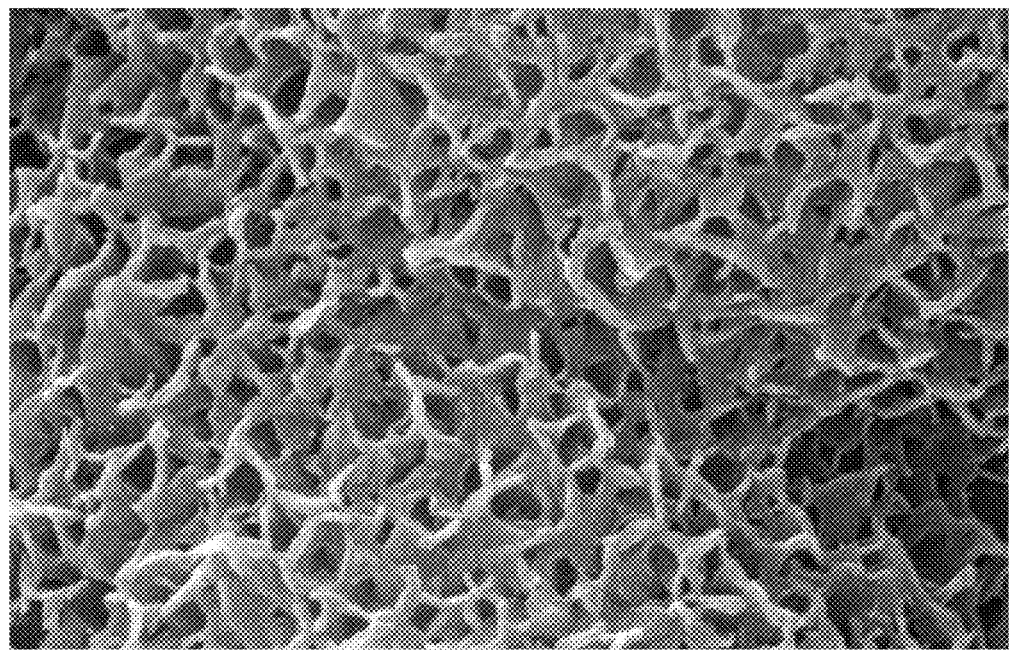
Figure 5:
FIGS. 5, 6, 7, 8A, 8B, 8C, and 8D are optical micrographs of cross sections of a scaffold of the invention subjected to histological staining.
Figure 6:
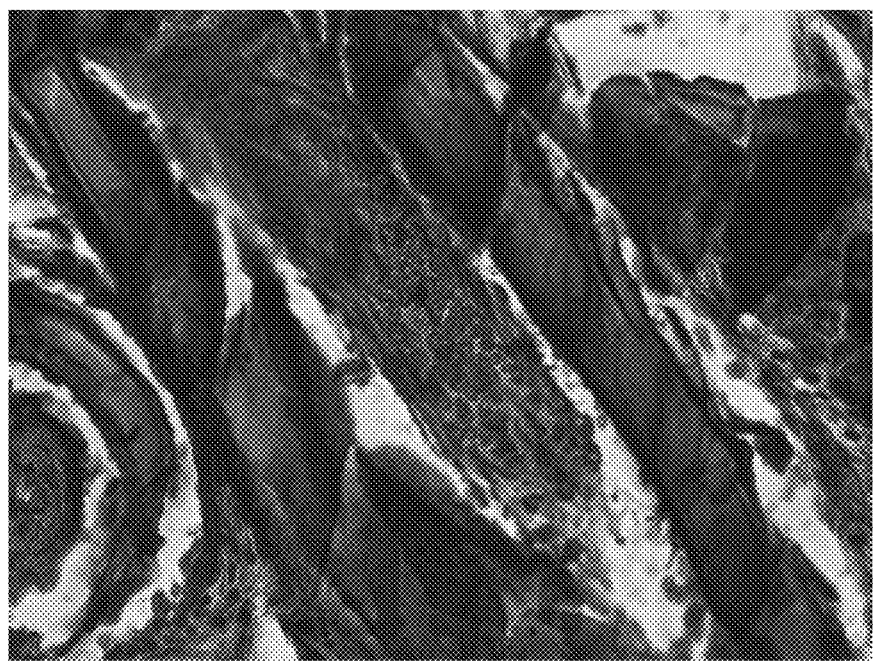
Figure 7:
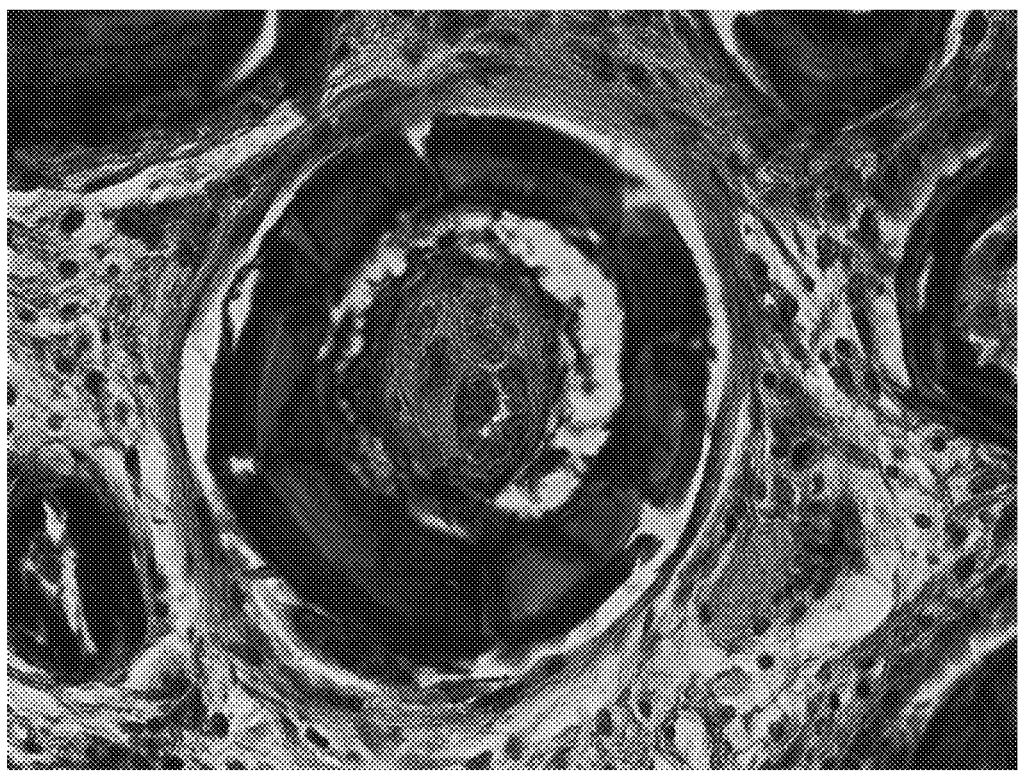
Figure 8A:
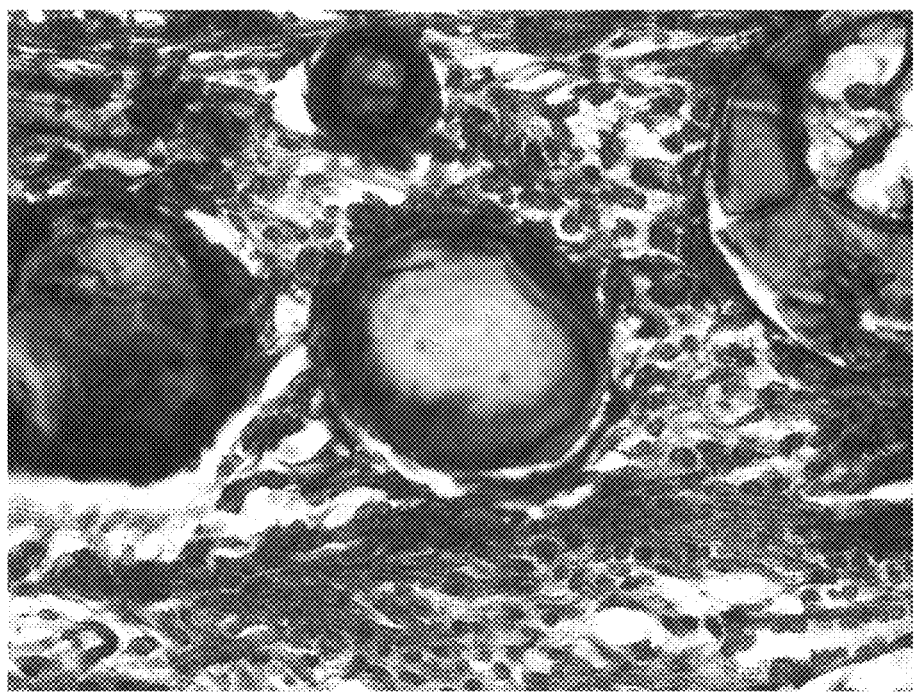
Figure 8B:
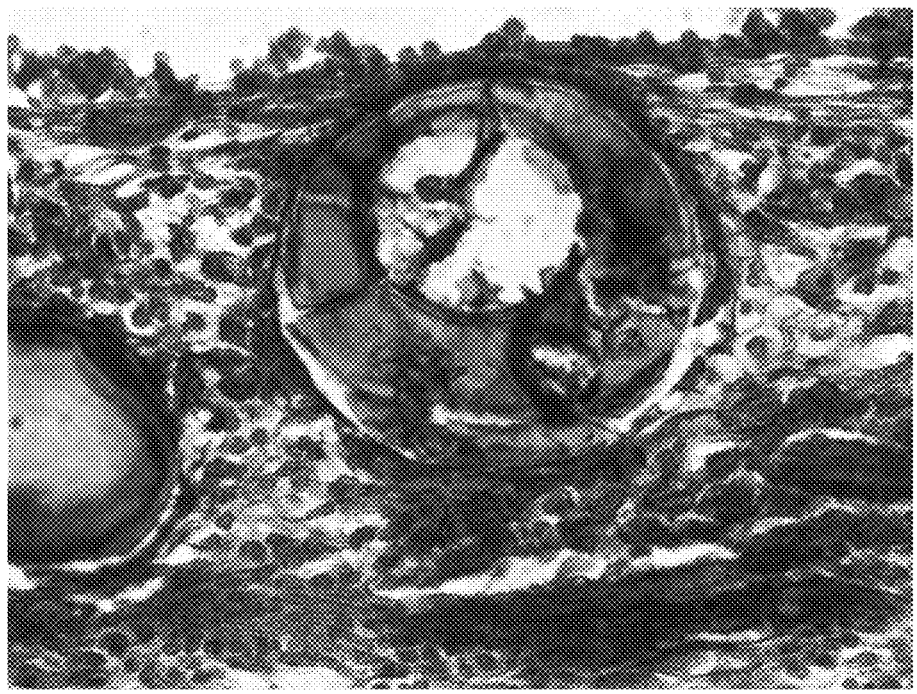
Figure 8C:
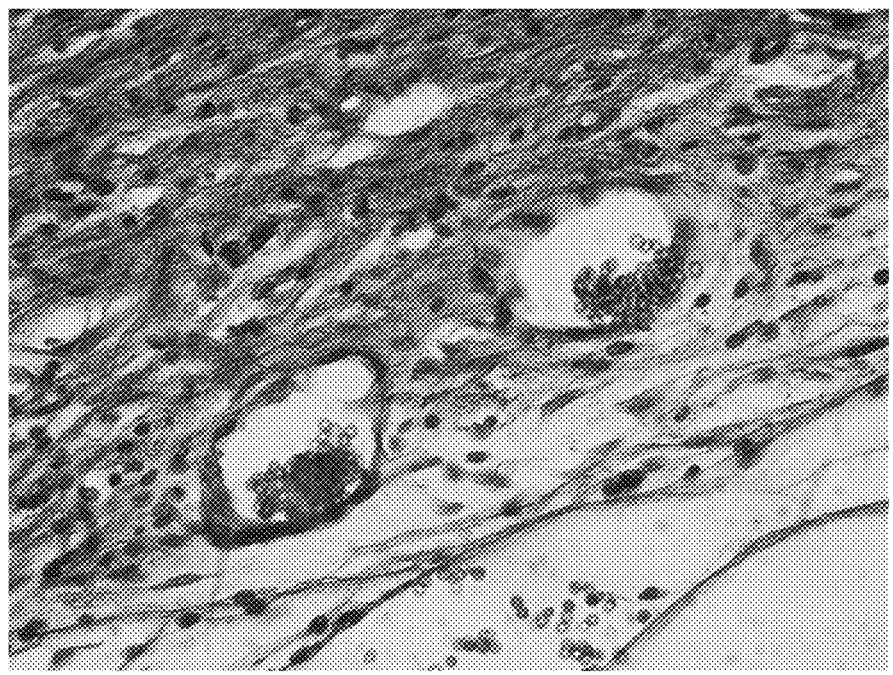
Figure 8D:
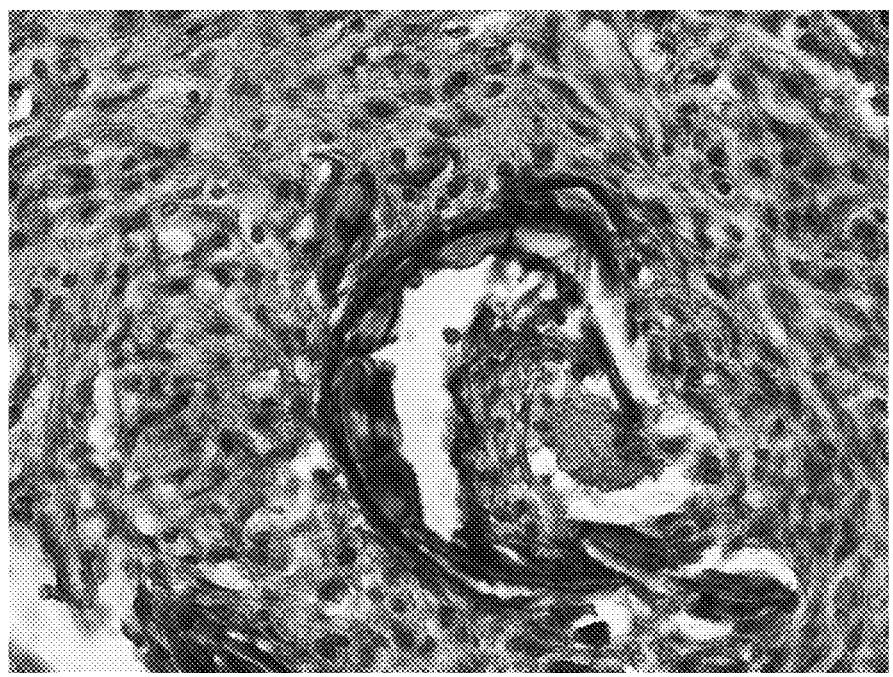
Figure 9A:
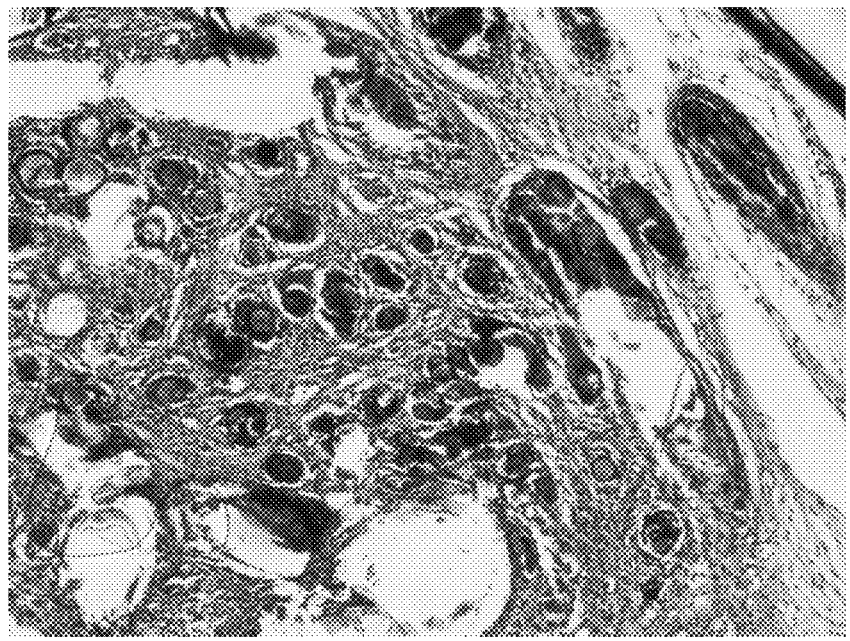
FIGS. 9A, 9B, 9C, 9D, 10A, 10B, 10C, and 10D are optical micrographs of cross sections of a scaffold employing prior art scaffold materials subjected to histological staining.
Figure 9B:
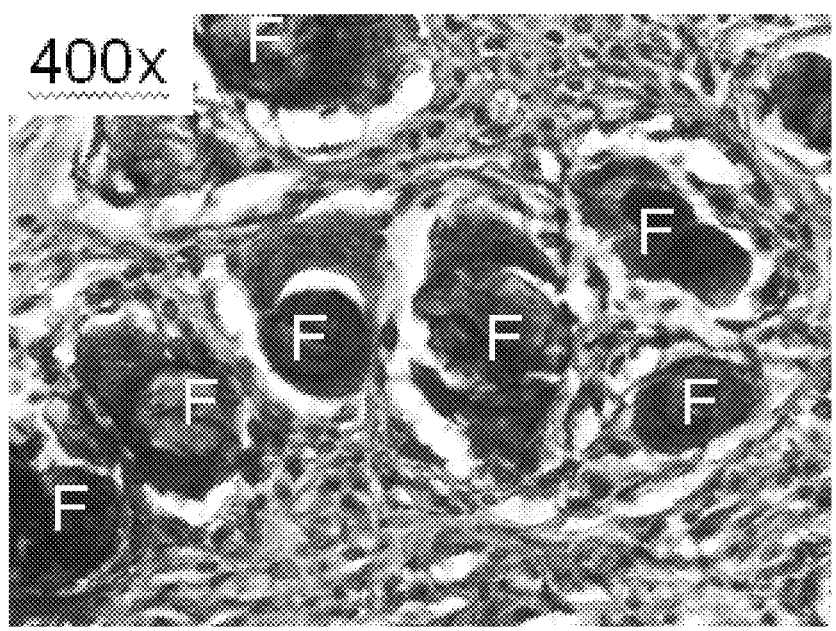
Figure 9C:
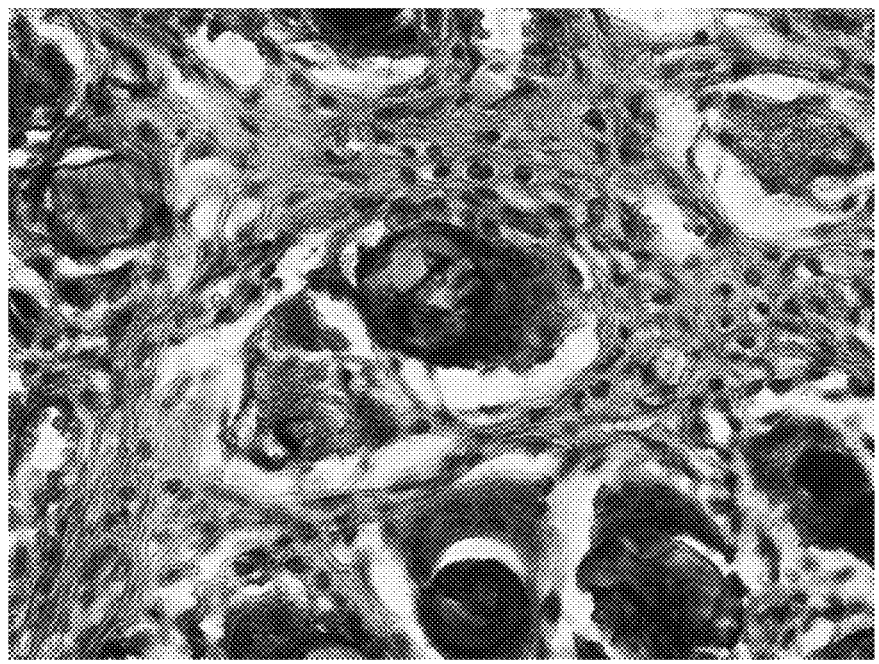
Figure 9D:
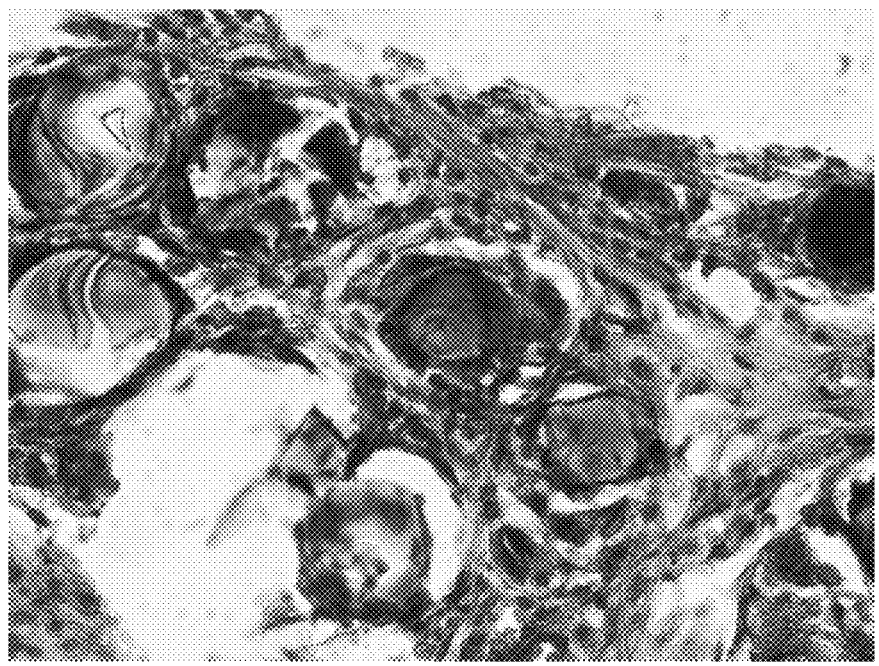
Figure 10A:
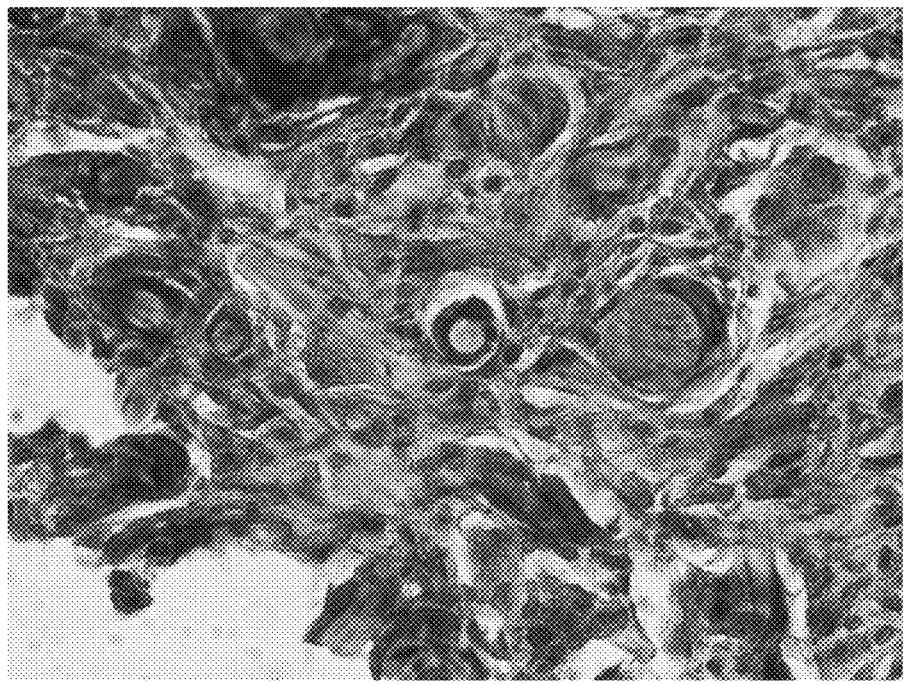
Figure 10B:
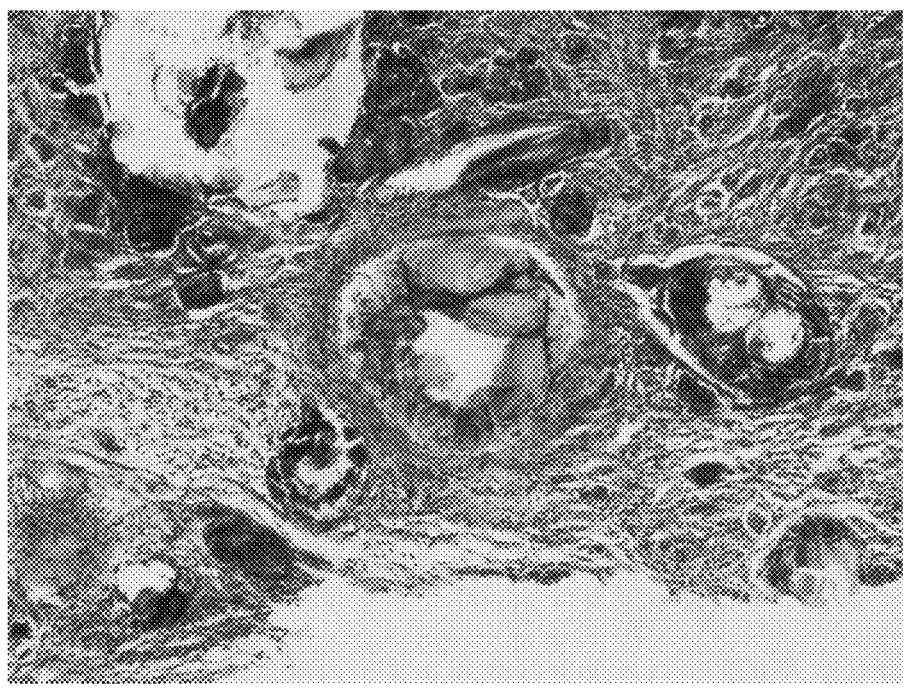
Figure 10C:
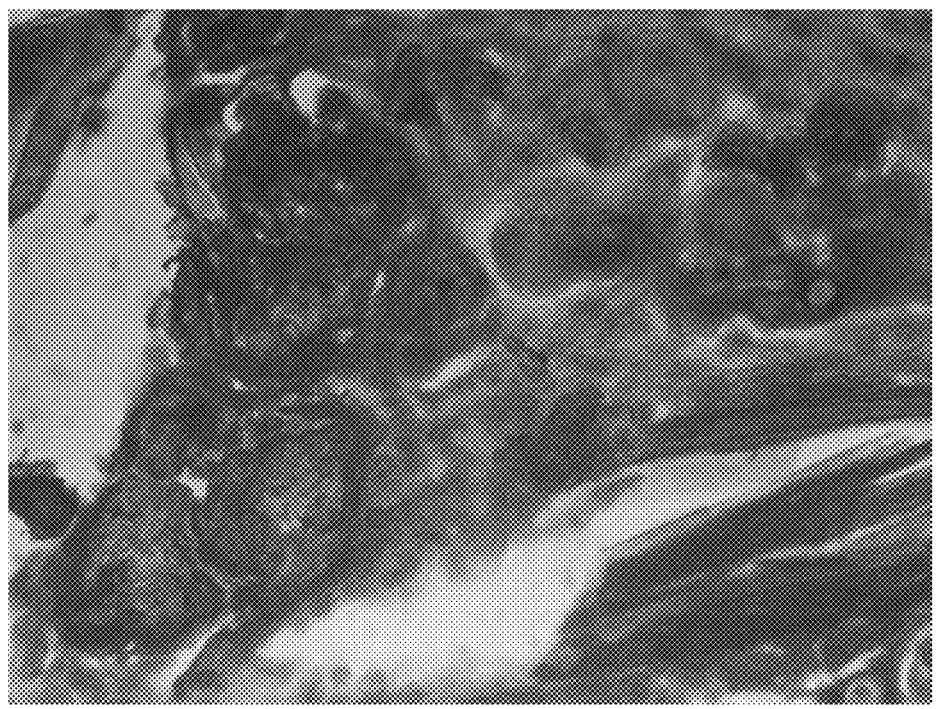
Figure 10D:
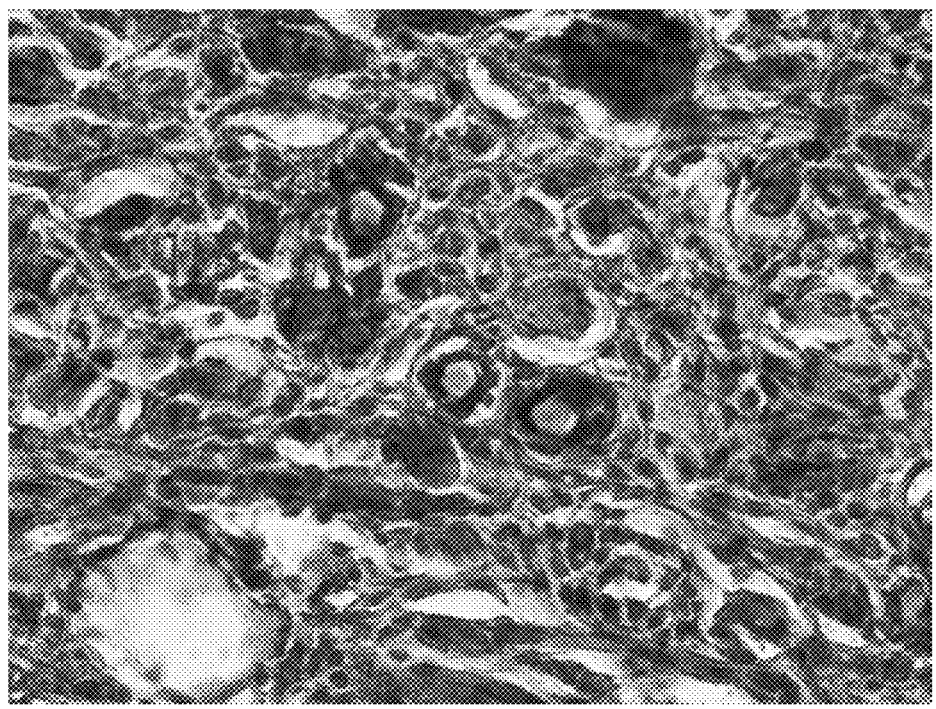

A cross section similar to that shown in FIGS. 3A and 3B having been removed from a rat after four weeks subcutaneous implantation was subjected to histological staining (H&E), and is shown in FIG. 5. This demonstrates biological compatibility between the tissue and the scaffold, the glass reaction with the body fluids which formed hollow fibers of HA and or ACP, and the tissue infiltration throughout the scaffold and into the hollow voids of the reacted fibers. A further cross section was taken in a direction parallel to the central longitudinal axis of a reacted fiber, and is shown in FIG. 6. The center of the photomicrograph shows substantial presence of red blood cells and soft tissue in the sectioned fiber. FIG. 7 is a further photomicrograph of a cross section taken in a direction perpendicular to the central axis of a fiber. Red blood cells, blood vessels, and soft tissue can be seen in the hollow core of the reacted glass fiber.

EXAMPLE 5

The immune response of the borate glass of the invention in comparison to prior art glasses was studied by H&E staining and examination of cross sections of respective scaffolds. The sections in FIGS. 8A, 8B, 8C, and 8D were taken of a scaffold of the invention after two weeks subcutaneous implantation in the back of a rat. These sections show healthy soft tissue growing between and attached to the glass fibers.

There are no giant cells visible close to the fibers. There are areas with good vascularization, which is important to the growth of new tissue. Stained sections of a prior art silicate-based bioactive glass known as 13-93 are shown in FIGS. 9A, 9B, 9C, and 9D, and almost all the fibers (e.g., F in 9B) have giant cells attached to and surrounding them.

The soft tissue penetrating the fibers appears healthy, but the giant cells surrounding the fibers are indicative of a foreign body response. A similar response to the 13-93 glass fibers occurs for prior art 45S5 glass fibers, as shown in FIGS. 10A, 10B, 10C and 10D. Nearly all the 45S5 fibers are surrounded by giant cells indicative of a foreign body response. The results shown in FIGS. 8A, 8B, 8C, 8D, 9A, 9B, 9C, 9D, 10A, 10B, 10C and 10D indicate that the material of invention has no significant immune response with soft tissue, and can convert to hydroxyapatite at a much faster rate than the silicate based bioactive glasses. This illustrates that the scaffold of the invention, when placed in contact with tissues containing body fluids, forms a porous hydroxyapatite material with a hollow core, which can fill with biological material such as hard and soft tissue (depending on the surrounding tissues), blood vessels, or possibly other tissues of the body. The histological assessment after implantation in subcutaneous soft tissue sites showed a minimal immune response to the surrounding and infiltrated soft tissue. It also appears to produce a smaller foreign body response than silicate based bioactive glasses such as 45S5 and 13-93.

EXAMPLE 6

In-vitro experiments were conducted to measure the reaction rates and the reaction products of the following Ca-free borate-based glasses (compositions in weight %):

TABLE III

| Wt. % Composition of Ca-Free Borate Glasses | | | | | |
|---|---|---|---|---|---|
| | $B_2O_3$ | $Na_2O$ | $Li_2O$ | MgO | BaO | Rxn Prods |
| I | 49.3 | 14.6 | | | 36.1 | $BaHPO_4$ |
| II | 78.7 | | 11.3 | 10 | | $Mg_3(PO_4)_2$ + ACP |
| III | 78.7 | | 11.3 | 10 | | |
| IV | 76 | | 11 | | 13 | $BaHPO_4$ |
| V | 59 | | 8 | | 33 | $BaHPO_4$ |
| VI | 45 | | 7 | | 48 | $Ba_3(PO_4)_2$ |

The compounds listed in the right hand column are reaction products after reacting particles of each glass in a 0.25 molar solution of $K_2HPO_4$ at 37 C for 108 to 130 hours.

EXAMPLE 7

Several borate-based glasses were prepared containing trace amounts of Cu, Sr, Zn, and Fe as oxides in various amounts according to the following concentrations:

| Trace Element Doped Borate Bioactive Glasses (wt %) | | | | | | | | | |
|---|---|---|---|---|---|---|---|---|---|
| Glass | $B_2O_3$ | $Na_2O$ | CaO | $K_2O$ | MgO | $P_2O_5$ | CuO | SrO | ZnO | $Fe_2O_3$ |
| 0 | 53.00 | 6.00 | 20.00 | 12.00 | 5.00 | 4.00 | | | | |
| 1 | 52.95 | 5.99 | 19.98 | 11.99 | 5.00 | 4.00 | 0.10 | | | |
| 2 | 52.89 | 5.99 | 19.96 | 11.98 | 4.99 | 3.99 | 0.20 | | | |
| 3 | 52.79 | 5.98 | 19.92 | 11.95 | 4.98 | 3.98 | 0.40 | | | |
| 4 | 52.47 | 5.94 | 19.80 | 11.88 | 4.95 | 3.96 | 1.00 | | | |
| 5 | 51.94 | 5.88 | 19.60 | 11.76 | 4.90 | 3.92 | 2.00 | | | |
| 6 | 51.73 | 5.86 | 19.52 | 11.71 | 4.88 | 3.90 | 0.40 | 2.00 | | |
| 7 | 51.20 | 5.80 | 19.32 | 11.59 | 4.83 | 3.86 | 0.40 | 2.00 | 1.00 | |
| 8 | 50.88 | 5.76 | 19.20 | 11.52 | 4.80 | 3.84 | 0.40 | 2.00 | 1.00 | 0.40 |

Scaffolds were prepared from glasses 0, 1, 2, 3, 4, and 5, which are depicted in FIGS. 12A, 12B, 12C, 12D, 12E, and 12F, respectively. These were implanted subcutaneously in the backs of rats, and examined for vascularization. FIGS. 13A, 13B, 13C, 13D, 13E, and 13F show the extent of vascularization after two weeks, and FIGS. 14A, 14B, 14C, 14D, 14E, and 14F after four weeks, for glasses 0 through 5, respectively. The effect of increasing Cu content on increasing vascularization is evident.

EXAMPLE 8

A blended fiber scaffold was prepared from a 50:50 by weight mixture of fibers of two distinct compositions:

| Glass Fiber Content | $B_2O_3$ | $Na_2O$ | CaO | $K_2O$ | MgO | $P_2O_5$ | CuO |
|---|---|---|---|---|---|---|---|
| 50% | 53.00 | 6.00 | 20.00 | 12.00 | 5.00 | 4.00 | |
| 50% | 52.47 | 5.94 | 19.80 | 11.88 | 4.95 | 3.96 | 1.00 |

EXAMPLE 9

The dissolution of boric acid in vivo is calculated. With a 53 wt % $B_2O_3$ glass and an exemplary scaffold mass of 0.070 g, the weight of $B_2O_3$ is 0.0371 g. The $B_2O_3$ dissolves into the bodily fluids and is present as $BO_3$ ions. For purpose of comparison to literature values, however, calculation here is made on the basis of $H_3BO_3$. The gravimetric factor of $B_2O_3$ to $H_3BO_3$ is 1.78, so the 0.0371 g of $B_2O_3$ dissolves into 0.066 g $H_3BO_3$, which corresponds to $1.07E^{-3}$ moles $H_3BO_3$. It was assumed, based on in vivo observations, that it takes four weeks for a $B_2O_3$ based scaffold of this size to completely react. This corresponds to $1.07E^{-3}/28$ days=$3.814E^{-5}$ moles/day $H_3BO_3$ yield. Prior observations also show that roughly 0.05 g of new tissue weight grows into a scaffold of this size. Prior observations also show that roughly between about 0.1 (minimum) and about 0.4 (maximum) ml/min of blood flows through a scaffold per gram of tissue. First assuming the minimum flow, the $H_3BO_3$ yield is calculated to have a concentration of 5.29 mM: 1440 min/day (0.1 ml/min*g)(1 day) (0.05 g)=7.2 ml=0.0072 L. $3.814E^{-5}$ moles/day $H_3BO_3$/0.0072 L=$5.29E^{-3}$ mol/L=5.29 mM $H_3BO_3$. Then assuming the maximum flow, the $H_3BO_3$ yield is calculated to have a concentration of 1.32 mM: 1440 min/day (0.4 ml/min/gram)=28.8 ml=0.0288 L. $3.814E^{-5}$ moles/day $H_3BO_3$/0.0288 L=$1.32E^{-3}$ mol/L=1.32 mM $H_3BO_3$. Based on data available in "Action of Boron at the Molecular Level", Bio. Trace Ele. Res., 85, 2002, $H_3BO_3$ in this concentration may stimulate RNA uptake. Accordingly, in sharp contrast to silicate-based scaffolds, the scaffolds of the invention upon dissolution naturally yield a substance which has been reported to function as a growth factor to enhance healing.

In view of the above, it will be seen that the several objects of the invention are achieved and other advantageous results attained.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above compositions and methods without departing from the scope of the invention, it is intended that all matter contained in the above description and shown in the accompanying drawings shall be interpreted as illustrative and not in a limiting sense.

The invention claimed is:

1. A three-dimensional scaffold with interconnected pores for repair of tissue comprising:
a scaffold body for structural support of the tissue scaffold comprising:
scaffold body components bonded to each other to define the scaffold body and provide a scaffold body compressive strength of greater than 5 MPa, wherein the scaffold body components are components in the form of fibers in combination with one or more components in the form of ribbons, solid spheres, hollow spheres, and particles, and the components are of a component material comprising, by approximate weight %:

| | |
|---|---|
| $B_2O_3$ | 40 to 90 |
| $Na_2O$ | 0 to 25 |
| $Li_2O$ | 0 to 25 |
| $K_2O$ | 0 to 25 |
| $Rb_2O$ | 0 to 25 |
| CaO | 0 to 40 |
| MgO | 0 to 25 |
| SrO | 0 to 40 |
| BaO | 0 to 50 |
| $P_2O_5$ | 0 to 10 |
| $SiO_2$ | 0 to 18 |
| $Al_2O_3$ | 0 to 3 |
| F | 0 to 4 |
| transition metal elements | 0 to 10 cumulative | wherein two or more of $Li_2O$, $Na_2O$, $K_2O$, and $Rb_2O$ are present in a cumulative concentration between about 1 and about 50 wt %, wherein two or more of MgO, SrO, BaO, and CaO are present in a cumulative concentration between about 1 and about 50 wt %, wherein the scaffold body has a porosity between about 15 and about 90 vol %.

2. The scaffold of claim 1 wherein the $B_2O_3$ concentration is between about 50 and about 90 wt %.

3. The scaffold of claim 1 wherein the $B_2O_3$ concentration is between about 60 and about 82 wt %.

4. The scaffold of claim 1 wherein:
the $B_2O_3$ concentration is between 50 and 90 wt %;
the component material comprises two or more oxides from among Li2O, $Na_2O$, $K_2O$, and $Rb_2O$ in a cumulative concentration between 5 and 25 wt % and two or more oxides from among MgO, SrO, BaO, and CaO in a cumulative concentration between 1 and 45 wt %; and
less than 5 wt % of the component material is crystalline material.

5. The scaffold of claim 1 wherein the scaffold body components contain MgO in a concentration is between about 1 and 25 wt %.

6. The scaffold of claim 1 wherein the scaffold body components contain $K_2O$ in a concentration is between about 1 and 25 wt % and MgO in a concentration is between about 1 and 25 wt %.

7. The scaffold of claim 1 wherein the component material comprises two or more oxides from among $Li_2O$, $Na_2O$, $K_2O$, and $Rb_2O$ in a cumulative concentration between 5 and 25 wt %.

8. The scaffold of claim 1 wherein the component material comprises two or more oxides from among $Li_2O$, $Na_2O$, $K_2O$, and $Rb_2O$ in a cumulative concentration between 5 and 25 wt % and two or more oxides from among MgO, SrO, BaO, and CaO in a cumulative concentration between 1 and 45 wt %.

9. The scaffold of claim 1 wherein the component material further comprises one or more elements selected from the group consisting of Zn, Cu, Fe, Mn, Si, Sr, Ni, Mo, and Se, in an amount between about 0.01 and 10 wt % per element and cumulatively less than 25 wt %.

10. The scaffold of claim 1 wherein the component material further comprises between about 0.01 and 10 wt % Cu as copper oxide.

11. A three-dimensional scaffold with interconnected pores for repair of tissue comprising:
a scaffold body for structural support of the tissue scaffold comprising:
scaffold body components bonded to each other to define the scaffold body and provide a scaffold body compressive strength of greater than 0.4 MPa, wherein the scaffold body components are of a component material comprising, by approximate weight %:

| | |
|---|---|
| B$_2$O$_3$ | 40 to 90 |
| Na$_2$O | 0 to 25 |
| Li$_2$O | 0 to 25 |
| K$_2$O | 0 to 25 |
| Rb$_2$O | 0 to 25 |
| CaO | 0 to 40 |
| MgO | 0 to 25 |
| SrO | 0 to 40 |
| BaO | 0 to 50 |
| P$_2$O$_5$ | 0 to 10 |
| SiO$_2$ | 0 to 18 |
| Al$_2$O$_3$ | 0 to 3 |
| F | 0 to 4 |
| transition metal elements | 0 to 10 cumulative | wherein two or more of Li$_2$O, Na$_2$O, K$_2$O, and Rb$_2$O are present in a cumulative concentration between about 1 and about 50 wt %, 0 wherein two or more of MgO, SrO, BaO, and CaO are present in a cumulative concentration between about 1 and about 50 wt %, wherein the scaffold body has a porosity between about 15 and about 90 vol %, and wherein at least 10 wt % of the scaffold body components have a first composition and at least 10 wt % of the scaffold body components have a second composition, wherein the first and second compositions are distinct from each other.

12. The scaffold of claim 1 wherein less than 5 wt % of the component material is crystalline material.

13. The scaffold of claim 1 wherein the component material, upon exposure to natural or simulated physiological phosphorus-containing fluids, does not react to form a crystalline or amorphous calcium phosphate.

14. The scaffold of claim 1 wherein the body components comprise the glass fibers and the particles.

15. The scaffold of claim 1 wherein the scaffold body consists essentially of the glass fibers and the one or more components in the form of ribbons, solid spheres, hollow spheres, and particles.

16. The scaffold of claim 1 wherein the scaffold body components consist essentially of 40 to 90 wt % B$_2$O$_3$, 1 to 25 wt % Na$_2$O, 1 to 25% K$_2$O, 1 to 40 wt % CaO, 1 to 25 wt % MgO, and 1 to 10 wt % P$_2$O$_5$.

17. The scaffold of claim 1 wherein the scaffold body components consist essentially of 40 to 90 wt % B$_2$O$_3$, 1 to 25 wt % Li$_2$O, and 1 to 40 wt % CaO.

18. The scaffold of claim 1 wherein the scaffold body components consist essentially of 40 to 90 wt % B$_2$O$_3$, 1 to 25 wt % Na$_2$O, and 1 to 40 wt % CaO.

19. The scaffold of claim 1 wherein the scaffold body components consist essentially of 40 to 90 wt % B$_2$O$_3$, 0.1 to 5% CuO, 1 to 25 wt % Na$_2$O, 1 to 25 wt % K$_2$O, 1 to 25 wt % MgO, and 1 to 10 wt % P$_2$O$_5$.

20. The scaffold of claim 1 wherein the scaffold body components consist essentially of the fibers and the particles.

21. The scaffold of claim 1 wherein the scaffold body components comprise the fibers and the solid spheres.

22. The scaffold of claim 1 wherein the compressive strength of the scaffold body is greater than 5 MPa and no more than 200 MPa.

23. The scaffold of claim 22 wherein the compressive strength of the scaffold body is between 20 and 200 MPa.

* * * * *

UNITED STATES PATENT AND TRADEMARK OFFICE
CERTIFICATE OF CORRECTION

| | | |
|---|---|---|
| PATENT NO. | : 9,561,250 B2 | Page 1 of 1 |
| APPLICATION NO. | : 13/936702 | |
| DATED | : February 7, 2017 | |
| INVENTOR(S) | : Delbert E. Day et al. | |

It is certified that error appears in the above-identified patent and that said Letters Patent is hereby corrected as shown below:

Column 1, Line 2 after the title and before the "FIELD OF THE INVENTION,"
please add the following paragraph:

--STATEMENT OF GOVERNMENT INTEREST
This invention was made with Government support under Department of the Army contract
W81XWH-08-1-0765. The Government may have certain rights in the invention.--

Signed and Sealed this
Twenty-sixth Day of September, 2017

Joseph Matal
*Performing the Functions and Duties of the*
*Under Secretary of Commerce for Intellectual Property and*
*Director of the United States Patent and Trademark Office*